(12) United States Patent
Schmidt et al.

(10) Patent No.: US 9,789,085 B2
(45) Date of Patent: Oct. 17, 2017

(54) METHODS OF TREATING DEMENTIA AND PHARMACEUTICAL COMPOSITIONS THEREOF

(71) Applicant: H. Lundbeck A/S, Copenhagen-Valby (DK)

(72) Inventors: Ellen Schmidt, Copenhagen K (DK); Johan Areberg, Limhamn (SE)

(73) Assignee: H. LUNDBECK A/S, Copenhagen-Valby (DK)

(*) Notice: Subject to any disclaimer, the term of this patent is extended or adjusted under 35 U.S.C. 154(b) by 0 days.

(21) Appl. No.: 15/194,947

(22) Filed: Jun. 28, 2016

(65) Prior Publication Data

US 2016/0354343 A1    Dec. 8, 2016

Related U.S. Application Data

(63) Continuation of application No. 14/021,033, filed on Sep. 9, 2013, now Pat. No. 9,375,418.

(60) Provisional application No. 61/782,084, filed on Mar. 14, 2013, provisional application No. 61/698,664, filed on Sep. 9, 2012.

(51) Int. Cl.
| | |
|---|---|
| *A61K 31/4045* | (2006.01) |
| *A61K 31/27* | (2006.01) |
| *A61K 31/445* | (2006.01) |
| *A61K 45/06* | (2006.01) |
| *A61K 31/55* | (2006.01) |
| *A61K 9/00* | (2006.01) |

(52) U.S. Cl.
CPC ........ *A61K 31/4045* (2013.01); *A61K 9/0053* (2013.01); *A61K 31/27* (2013.01); *A61K 31/445* (2013.01); *A61K 31/55* (2013.01); *A61K 45/06* (2013.01)

(58) Field of Classification Search
None
See application file for complete search history.

(56) References Cited

U.S. PATENT DOCUMENTS

| | | |
|---|---|---|
| 3,597,149 A | 8/1971 | Masuda et al. |
| 5,070,096 A | 12/1991 | Mohrs et al. |
| 5,093,340 A | 3/1992 | Mohrs et al. |
| 5,202,336 A | 4/1993 | Mohrs et al. |
| 6,187,805 B1 | 2/2001 | Pineiro et al. |
| 6,750,348 B1 | 6/2004 | Bridger et al. |
| 7,157,488 B2 | 1/2007 | Chen et al. |
| 8,044,090 B2 | 10/2011 | Chen et al. |
| 2007/0099909 A1 | 5/2007 | Chen et al. |
| 2009/0306110 A1 | 12/2009 | Chen et al. |
| 2012/0184532 A1 | 7/2012 | Franklin et al. |
| 2014/0073681 A1 | 3/2014 | Schmidt et al. |
| 2016/0256437 A1 | 9/2016 | Schmidt et al. |

FOREIGN PATENT DOCUMENTS

| | | |
|---|---|---|
| CZ | 105267 | 4/1962 |
| CZ | 105995 | 6/1962 |
| CZ | 105955 | 12/1962 |
| FR | 2181559 | 12/1973 |
| GB | 2085006 | 4/1982 |
| WO | WO-93/11761 | 6/1993 |
| WO | WO-95/06638 | 3/1995 |
| WO | WO-95/30655 | 11/1995 |
| WO | WO-99/16746 | 4/1999 |
| WO | WO-00/34242 | 6/2000 |
| WO | WO-00/42045 | 7/2000 |
| WO | WO-02/078693 | 10/2002 |
| WO | WO-2007/087151 | 8/2007 |
| WO | WO-2007/147883 | 12/2007 |
| WO | WO-2008/002539 | 1/2008 |
| WO | WO-2011/076212 | 6/2011 |

OTHER PUBLICATIONS

"Lundbeck-Otsuka Alzheimer's Candidate Fails Phase III Trial," Genetic Engineering & Biotechnology News <http://www.genengnews.com/print/42640> 2 pages (2016).
H. Lundbeck A/S, "Headline conclusions from the first out of three phase III studies on idalopirdine in Alzheimer's disease," Corporate Release No. 600, 3 pages (2016).
Alzheimer's Society, Factsheet 407LB, "Drug treatments for Alzheimer's disease," Updated Mar. 2012, downloaded from "alzheimers.org.uk" on Nov. 23, 2013, pp. 1-11.
Ambrose, "Altered drug action with aging," Health Notes, vol. 1(7), pp. 12-15 (2003).
Arnt et al., "Lu AE58054, a 5-HT6 antagonist, reverses cognitive impairment induced by subchronic phencyclidine in a novel object recognition test in rats," International Journal of Neuropsychopharmacology 13 pp. 1021-1033 (2010).
Barton et al., "866. Phenol Oxidation and Biosynthesis. Part VI. The Biogenesis of Arnaryllidaceae Alkaloids," Journal of the Chemical Society, pp. 4545-4558 (1963).
Bos et al., "5-HT6 Receptor antagonists: lead optimization and biological evaluation of N-aryl and N-heteroaryl 4-amino-benzene sulfonamides," Eur. J. Med. Chem., vol. 36, pp. 165-178 (2001).
Bourson et al., "Determination of the Role of the 5-HT6 receptor in the Rat Brain: A Study using Antisense Oligonucleotides," J. of Pharm. and Experimental Therapeutics, vol. 274, No. 1, pp. 173-180 (1995).
Bromidge et al., "Phenyl Benzenesulfonamides are Novel and Selective 5-HT6 Antagonists: Identification of N-(2,5-dibromo-3-fluorophenyl)-4-methoxy-3-piperazin-1-ylbenzenesulfonamide (SB-357134)," Bioorganic & Medicinal Chemistry Letters, vol. 1, pp. 55-58 (2001).
CAS Registry No. 302795-49-9, 2 pages (2005).
Clinical Trials.Gov, "Efficacy Study Exploring the Effect of Lu AE58054 as Augmentation Therapy in Patients With Schizophrenia," First Received Dec. 17, 2008; Last verified Aug. 2012 (4 pages).

(Continued)

*Primary Examiner* — Savitha Rao
*Assistant Examiner* — Gregg Polansky
(74) *Attorney, Agent, or Firm* — Wilmer Cutler Pickering Hale and Dorr LLP

(57) ABSTRACT

The present invention describes methods of treating dementia comprising administering an effective daily dose of N-[2-(6-fluoro-1H-indol-3-yl)ethyl]-3-(2,2,3,3-tetrafluoropropoxy)benzylamine to improve or augment the effect of an acetylcholinesterase inhibitor.

22 Claims, 13 Drawing Sheets

(56) References Cited

OTHER PUBLICATIONS

Codony et al., "5-HT6 receptor and cognition," Current Opinion in Pharmacology, vol. 11, No. 1, pp. 94-100 (2011).
Falcone et al., "Identification of LY483518 as a Potent and Selective 5-HT6 Receptor" Program No. 586.9, 2002 Neuroscience Meeting Planner. Orlando, FL: Society for Neuroscience, 2 pages (2002).
Glennon et al., "5-HT6 Serotonin Receptor Binding of Indolealkylamines: A Preliminary Structure-Affinity Investigation," Med. Chem. Res., vol. 9, pp. 108-117 (1999).
Glennon et al., "Influence of Amine Substituents on 5-HT2A versus 5-HT2C Binding of Phenylakllyl- and Indolylalkylamines," J. Med. Chem. vol. 37, pp. 1929-1935 (1994).
U.S. Department of Health and Human Services Food and Drug Administration Center for Drug Evaluation and Research (CDER) "Guidance for Industry: Estimating the Maximum Safe Starting Dose in Initial Clinical Trials for Therapeutics in Adult Healthy Volunteers," 30 pages (Jul. 2005).
Ide and Buck, "Pharmacologically Active Compounds from Alkoxy-B-Phenylethylamines," JACS, pp. 726-732 (1937).
International Search Report for International Application No. PCT/EP2013/068516 dated Nov. 19, 2013 (5 pages).
Isaac et al., "6-Bicyclopipereazinyl-1-arylsulfonylindoles and 6-Bicyclopiperidinyl-1-arylsulfonylindole Derivatives as Novel, Potent, and Selective 5-HT6 Receptor Antagonists," Bioorganic & Medicinal Chemistry Letters, pp. 1719-1721 (2000).
Lundbeck Press Release No. 472, 4 pages (May 29, 2012).
Marcos et al., "Effects of 5-HT6 receptor antagonism and cholinesterase inhibition in models of cognitive impairment in the rat," British Journal of Pharmacology, vol. 155, No. 3, pp. 434-440 (2008).
Meneses, "Effects of the 5-HT6 receptor antagonist Ro 04-6790 on learning consolidation," Behavioral Brain Research, vol. 1818, pp. 107-110 (2001).
Mitchell et al., "5-HT6 Receptor Ligands as Anti-dementia Drugs," International Review of Neurobiology, Academic Press, London, GB, vol. 96, pp. 163-187 (2011).
Neale et al., "A 14 Day, Dose Escalation, Double Blind, Randomized, Placebo-Controlled Study of SGS518 in Adult Patients with Schizophrenia," Neuropsychopharmacology 30:S54, 1 page (2005).
Rogers et al., "5-HT6 receptor antagonists enhance retention of a water maze task in the rat," Psychopharmacology, vol. 158, 114-119 (2001).
Tsai et al., "N1-(Benzenesulfonyl)typtamines as Novel 5-HT6 Antagonists," Bioorganic & Medicinal Chemistry Letters, pp. 55-58 (2001).
Vinogradova et al., "Synthesis based on β-Phenylethylamines. IV. Synthesis and Antiarrhythmic Activity of Substituted Phenylalkylamines and N-Benzyltetrahydroisoquinolines" Chemistry of Natural Compounds, vol. 29, No. 3, pp. 259-414 (1993).
Vinogradova and Nabiev "Syntheses Based on β-Ethylamines. VIII. Synthesis of Substituted 2-Benzyltetrahydroisoquinolines and their Influence on Bile Secretion," Chemistry of Natural Compounds, vol. 30, No. 3, pp. 368-370 (1994).
Wilkinson et al., "A Clinical Phase II Study of Lu AE58054 Added to Stable Donepezil Treatment in Patients with Moderate Alzheimer's Disease," Alzheimer's & Dementia: The Journal of the Alzheimer's Association, vol. 9, Issue 4, Supplement, p. P529 (2013).
Wolff et al., "5-HT6 Receptor Antagonists Enhance Memory in Radial Maze and Object Recognition Tasks," Program No. 586.1, 2002 Neuroscience Meeting Planner. Orlando, FL: Society for Neuroscience, 2 pages (2002).
Written Opinion for International Application No. PCT/EP2013/068516 dated Mar. 9, 2015 (7 pages).

METHODS OF TREATING DEMENTIA AND PHARMACEUTICAL COMPOSITIONS THEREOF

This application is a continuation of U.S. patent application Ser. No. 14/021,033, filed Sep. 9, 2013, which claims priority to U.S. Provisional Application Ser. No. 61/782,084, filed Mar. 14, 2013, and 61/698,664, filed Sep. 9, 2012.

FIELD OF THE INVENTION

The present invention describes methods of treating Alzheimer's disease comprising administering an effective dose of Compound I to improve or augment the effect of an acetylcholinesterase inhibitor such as donepezil or rivastigmine. The invention further provides pharmaceutical compositions comprising Compound I.

BACKGROUND ART

Dementia is a clinical syndrome characterized by deficits in multiple areas of cognition that cannot be explained by normal aging, a noticeable decline in function, and an absence of delirium. In addition, neuropsychiatric symptoms and focal neurological findings are usually present. Dementia is further classified based on etiology. Alzheimer's disease (AD) is the most common cause of dementia, followed by mixed AD and vascular dementia, vascular dementia, Lewy body dementia (DLB), and fronto-temporal dementia.

The incidence of Alzheimer's disease is expected to increase through the year 2050 with an estimated prevalence of 11 to 16 million cases. Currently, two classes of medications are FDA approved for managing symptoms of AD—acetylcholinesterase inhibitors (AChEIs) and an N-methyl-D-aspartase (NMDA) receptor antagonist. AChEIs are commonly used as initial treatment on diagnosis. The AChEIs—donepezil, rivastigmine, galantamine, and tacrine—are indicated for mild-to-moderate AD; only donepezil is approved for the severe stage.

Despite the available therapies, there are no treatments to cure AD or to prevent or stop disease progression. Acetylcholinesterase inhibitors do not help everyone who has Alzheimer's disease and in fact are not efficacious in many patients. Considering that AChEIs and memantine have only a modest symptomatic effect, and cannot prevent AD decline and slow disease progression, there is a high unmet need for more effective symptomatic treatments and for a disease modifying/slowing therapies.

The use of selective 5-HT$_6$ receptor antagonists to treat cognitive dysfunction has been suggested and is based on several lines of reasoning. For example, selective 5-HT$_6$ receptor antagonists have been shown to modulate cholinergic and glutamatergic neuronal function. The activity of selective 5-HT$_6$ receptor antagonists has been demonstrated in animal models of cognitive function. Since the disclosure of the first selective 5-HT$_6$ receptor antagonists, there have been several reports on the activity of these selective compounds in in-vivo models of cognitive function. N-[2-(6-fluoro-1H-indol-3-yl)ethyl]-3-(2,2,3,3-tetrafluoropropoxy)benzylamine (herein referred to as "Compound I") is a potent and selective 5-HT$_6$ receptor antagonist which has been in clinical development for treating cognition impairment associated with schizophrenia and as a treatment for AD.

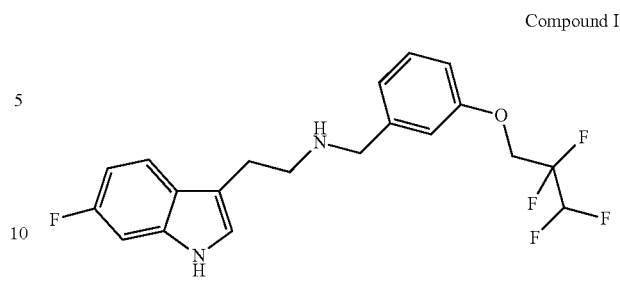

Compound I

In November 2008, a multi-centre, randomised, double-blind, fixed-dose study (120 mg/day BID) was initiated to explore the efficacy and safety of Compound I as adjunctive treatment to risperidone in patients with schizophrenia. Overall improvement in schizophrenia symptoms was assessed by using the Positive and Negative Syndrome Scale (PANSS) total score. Compound I did not offer any treatment advantage over placebo as measured by the PANSS total score. In 2010, it was announced that there did not appear to be any treatment advantage over placebo in improving patients' overall neurocognitive performance as assessed using the BACS composite Z-score and the PANSS cognitive subscale scores.

In 2012, it was reported that a randomized, double blind, placebo controlled trial conducted in Europe, Canada and Australia met its primary endpoint in the treatment of AD. Data demonstrated that Compound I plus 10 mg/day of donepezil significantly improved cognitive function in 278 patients with Alzheimer's disease compared to placebo plus donepezil, when measured by Alzheimer's Disease Assessment Scale-cognitive sub-scale (ADAS-cog). Compound I showed positive results in secondary endpoints including measures of global impression and daily living activities compared to donepezil treated patients.

The daily dose of 90 mg of Compound I in the AD study was administered three times daily (3×30 mg) to overcome the relative short half-life observed in subjects in previous clinical studies. An issue for that dose selection was to ensure that the maximum exposure level fell under the maximum exposure limit which had been established from non-clinical toxicology studies. Accordingly, a fixed dose of three times in the study was introduced.

As the 5-HT$_6$ receptor is a novel target predominately localized in the brain, a key problem in the development is to determine the amount of CNS penetration and the correlation with plasma exposure.

With CNS targets, further challenges exist that revolve around whether a drug will pass the blood brain barrier and whether it will reach the target at a suitable concentration and for a sufficient length of receptor occupancy.

Direct brain measures of 5-HT$_6$ receptor occupancy may be valuable to many decision-making processes during the development of centrally acting drugs targeted at 5-HT$_6$ to ensure adequate proof-of-concept testing and to optimize dosing regimens. In humans, tools such as positron emission tomography (PET) with specific radiolabeled ligands have been used to quantitatively assess in-vivo occupancy of a number of neurotransmitter receptors, including those for dopamine, serotonin, and benzodiazepines (Talbot, et al., European Neuropsychopharmacology, 2002, 12, 503-511).

The inventors discovered an effective PET ligand, [$^{11}$C]-LuPET, which has since been successfully evaluated for human use. The ligand was subsequently used to determine the 5-HT$_6$ receptor occupancy following multiple dose ranges of Compound I. In the assessment for receptor occupancy, human subjects were administered the compound for at least three days at several dosage regimens.

The inventors discovered that high levels of receptor occupancies were observed after multiple dosages of Compound I and that receptor occupancy was maintained 24 hrs post dose. Data generated from a separate Phase I PK study in the elderly and data generated from the above AD study have shown that the elimination half life of Compound I in the elderly population was longer (about 19 hours) compared to young healthy subjects (about 12 hours).

With these convergent discoveries, the inventors have identified improved methods of treating AD by introducing a new and improved dosage regime comprising once daily administration in a novel dosage range. Based on the findings described herein, the dose range contemplated is expected to be efficacious while providing exposure levels below the NOAEL, thus improving the safety ratio. The invention is described in described in greater detail below.

SUMMARY OF THE INVENTION

There remains a need for new treatments and therapies for Alzheimer's disease, and Alzheimer's disease-related disorders, such as dementia.

Thus, provided herein are methods of treating Alzheimer's disease as adjunctive therapy to treatment with an acetylcholinesterase inhibitor comprising administering an effective daily dose of N-[2-(6-fluoro-1H-indol-3-yl)ethyl]-3-(2,2,3,3-tetrafluoropropoxy)benzylamine or a pharmaceutically acceptable salt to a patient in need of such treatment, wherein the effective daily dose administered to the patient is between about 30 and about 60 mg.

The invention further provides methods of treating Alzheimer's disease as adjunctive therapy to treatment with an acetylcholinesterase inhibitor comprising administering an effective daily dose of N-[2-(6-fluoro-1H-indol-3-yl)ethyl]-3-(2,2,3,3-tetrafluoropropoxy)benzylamine or a pharmaceutically acceptable salt to a patient in need of such treatment, wherein the effective daily dose administered to the patient is between about 30 and about 60 mg.

One embodiment of the invention is directed to a method of treating mild to moderate Alzheimer's disease. In one embodiment, the pharmaceutically acceptable salt is the hydrochloride.

In another embodiment, the dose is administered as an immediate release formulation.

Yet another embodiment, the method is for treating mild to moderate Alzheimer's disease.

In another embodiment, the acetylcholinesterase inhibitor is donepezil.

In another embodiment, the acetylcholinesterase inhibitor is rivastigmine.

In another embodiment, the dose is administered once daily.

The aforementioned embodiment of the invention pertaining to once daily administration of Compound I has clear advantages for patients. Such advantages include but are not limited to ease of administration, convenience, and patient compliance with consistent dosing. However, certain embodiments of the invention also include, based on the Applicants' data herein, administration of Compound I more than once daily in amounts equivalent to the amounts disclosed herein within a twenty-four hour period.

Thus, embodiments of the invention also include the following:

In one embodiment, the effective daily dose is 30 mg.

In yet another embodiment, the dose is effective daily dose is 40 mg or less.

In one embodiment, the dose is effective daily dose is 50 mg or less.

In another embodiment, the dose is effective daily dose is 60 mg or less.

As used herein, Compound I is N-[2-(6-fluoro-1H-indol-3-yl)ethyl]-3-(2,2,3,3-tetrafluoropropoxy)benzylamine and accordingly, the invention further provides a pharmaceutical composition comprising Compound I wherein the composition when administered to a human provides a blood plasma concentration of Compound I in a range of about 56 ng/mL to about 310 ng/mL at steady-state plasma level and when the composition is administered to provide an effective daily dose of Compound I of about 60 mg or less.

Further provided is a pharmaceutical composition comprising Compound I wherein the composition provides when administered to a human a receptor occupancy of Compound I greater than or equal to about 90% at the 5HT-6 receptor at a steady-state plasma level and when the composition is administered to provide an effective daily dose of Compound I of about 60 mg of less.

The invention further provides a pharmaceutical composition comprising 60 mg or less of Compound I, wherein the composition when administered to a human provides a blood plasma concentration of Compound I in a range of about 56 ng/mL to about 310 ng/mL at steady-state plasma level.

In one embodiment, the composition is an immediate release formulation.

In one embodiment, the effective daily dose is 30 mg.

In yet another embodiment, the effective daily dose is 40 mg or less.

In one embodiment, the effective daily dose is 50 mg or less.

The invention describes novel methods for treating and preventing dementia caused by vascular diseases; dementia associated with Parkinson's disease; Lewy Body dementia; AIDS dementia; mild cognitive impairments; age-associated memory impairments; cognitive impairments and/or dementia associated with neurologic and/or psychiatric conditions, including epilepsy, brain tumors, brain lesions, multiple sclerosis, Down's syndrome, Rett's syndrome, progressive supranuclear palsy, frontal lobe syndrome, and schizophrenia and related psychiatric disorders; cognitive impairments caused by traumatic brain injury, post coronary artery by-pass graft surgery, electroconvulsive shock therapy, and chemotherapy, comprising administering a therapeutically effective amount of N-[2-(6-fluoro-1H-indol-3-yl)ethyl]-3-(2,2,3,3-tetrafluoropropoxy)benzylamine to improve or augment the effect of a acetylcholinesterase inhibitor.

The invention also describes novel methods for treating and preventing delirium, Tourette's syndrome, myasthenia gravis, attention deficit hyperactivity disorder, autism, dyslexia, mania, depression, apathy, and myopathy associated with or caused by diabetes comprising administering a therapeutically effective amount of N-[2-(6-fluoro-1H-indol-3-yl)ethyl]-3-(2,2,3,3-tetrafluoropropoxy)benzylamine to improve or augment the effect of a acetylcholinesterase inhibitor. The invention further describes novel methods for delaying the onset of Alzheimer's disease, for enhancing cognitive functions, for treating and preventing sleep apnea, for alleviating tobacco withdrawal syndrome, and for treating the dysfunctions of Huntington's disease comprising administering a therapeutically effective amount of N-[2-(6-fluoro-1H-indol-3-yl)ethyl]-3-(2,2,3,3-tetrafluoropropoxy)benzylamine to improve or augment the effect of a cholinesterase inhibitor.

Provided herein are methods of treating Alzheimer's disease by improving or augmenting the effect of a acetylcholinesterase inhibitor comprising administering a dose of N-[2-(6-fluoro-1H-indol-3-yl)ethyl]-3-(2,2,3,3-tetrafluoropropoxy)benzylamine at least once daily. In one embodiment, the dose is administered every two days.

The invention is described in more detail below.

DETAILED DESCRIPTION OF THE INVENTION

Figure 1:
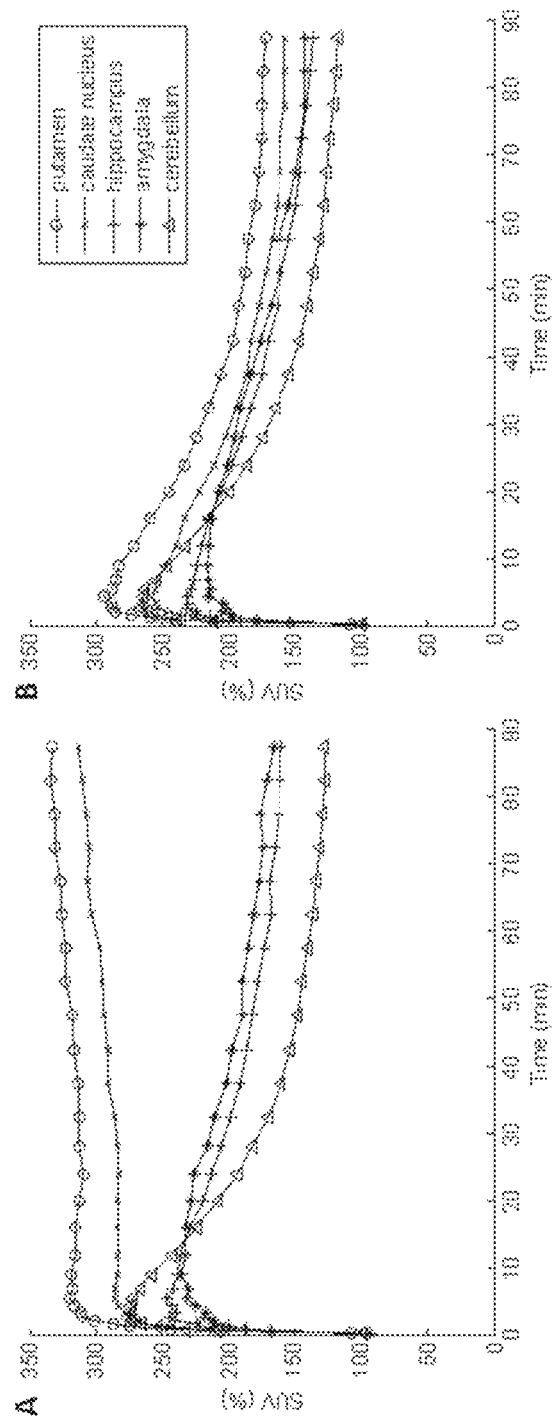
FIG. 1: Time-activity curves (TACs) of selected brain regions.

Prior to setting forth the invention in detail, it may be helpful to provide definitions of certain terms to be used herein. Unless defined otherwise, all technical and scientific terms used herein have the same meaning as is commonly understood by one of skill in the art to which this invention belongs.

N-[2-(6-fluoro-1H-indol-3-yl)ethyl]-3-(2,2,3,3-tetrafluoropropoxy)benzylamine is a potent and selective 5-HT$_6$ receptor antagonist in clinical development for treating AD and is referred to as Compound I. The synthesis of Compound I, its use for the treatment of cognitive dysfunction disorders, and pharmaceutical compositions comprising this substance are disclosed in U.S. Pat. No. 7,157,488. Unless otherwise specified, or clearly indicated by the text, reference to Compound I useful in the therapy of the invention includes both the free base and all pharmaceutically acceptable salts of the compounds. A preferred salt of Compound I is the hydrochloride.

The AD study cited in the Background section is referred to in this application as study 12936 The schizophrenia study cited in the Background section is referred to in this application as study 12450A.

In one embodiment of the invention, provided herein are methods of treating Alzheimer's disease by improving or augmenting the effect of a acetylcholinesterase inhibitor comprising administering a once daily effective dose of N-(2-(6-fluoro-1H-indol-3-yl)ethyl-3-(2,2,3,3-tetrafluoropropoxy)benzylamine or a pharmaceutically acceptable salt to a patient in need of treatment thereof, wherein the dose range is between about 30 and about 60 mg. The invention further provides methods of treating AD Alzheimer's disease with Compound I as adjunctive therapy to acetylcholinesterase inhibitors.

One embodiment of the invention is directed to methods of treating mild Alzheimer's disease while a separate embodiment relates to methods of treating moderate Alzheimer's disease.

Yet another embodiment relates to methods of treating severe Alzheimer's disease.

One embodiment relates to methods of treating mild to moderate Alzheimer's disease.

In one embodiment, Compound I is administered as an immediate release formulation.

In another embodiment, Compound I is administered as a pharmaceutically acceptable salt.

In one embodiment, Compound I is administered as the hydrochloride salt.

In one embodiment, the acetylcholinesterase inhibitor is donepezil.

In another embodiment, the acetylcholinesterase inhibitor is rivastigmine.

In yet another embodiment, the acetylcholinesterase inhibitor is galantamine.

In one embodiment, the dose is an amount between 10 and 80 mg.

In a separate embodiment, the dose is an amount between 10 and 70 mg.

In one embodiment, the dose is an amount between 10 and 60 mg.

In one embodiment, the dose is an amount between 10 and 50 mg.

In one embodiment, the dose is an amount between 20 and 50 mg.

In one embodiment, the dose is an amount between 20 and 40 mg.

In a separate embodiment, the compound is administered in a 10 mg dose.

In one embodiment, Compound I administered in a 20 mg dose.

In one embodiment, Compound I is administered in a 30 mg dose.

In one embodiment, Compound I is administered in a 40 mg dose.

In another embodiment, Compound I is administered in a 50 mg dose.

In one embodiment, Compound I is administered in a 60 mg dose.

In yet another embodiment, Compound I is administered in a 70 mg dose.

In one embodiment, Compound I administered in a 80 mg dose.

In one embodiment, Compound I is administered in a 90 mg dose.

As used herein, the following terms shall have the meanings as set forth below:

A "therapeutically effective dose" of Compound I is an amount sufficient to provide an observable therapeutic benefit compared to baseline clinically observable signs and symptoms of Alzheimer's disease as measured by ADAS-cog, and Alzheimer's disease-related dementia treated in connection with the combination therapy.

"Immediate-release" is meant to include a conventional release, in which release of the drug starts immediately after administration. As used herein, the term "immediate release" includes dosage forms that allow the drug to dissolve in the gastrointestinal contents, with no intention of delaying or prolonging the dissolution or absorption of the drug. The objective is for the drug to be released rapidly after administration, for example for it to be possible to release at least 80% of the anti-dementia drug within approximately 30 minutes after commencement of dissolution in a dissolution test.

The term "acetylcholinesterase inhibitor" is known in those skilled in art and includes compounds selected from the group consisting of donepezil, rivastigmine, galantamine and tacrine. The FDA approved dosages of the acetylcholinesterase inhibitor are encompassed by the instant invention. For example, the methods cover the dosages of donepezil shown to be effective in controlled clinical trials of the treatment of mild to moderate Alzheimer's disease are 5 mg or 10 mg administered orally once per day. A 23 mg orally once daily dose of donepezil is also approved for treating moderate to severe AD.

The term "steady-state plasma level" means that a plasma level for Compound I has been achieved and which is maintained with subsequent doses of Compound I (preferably Css is maintained) at a level which is at or above the minimum effective therapeutic level and is below the minimum toxic plasma level for a given active agent(s).

The term "daily" means a given, continuous twenty-four (24) hour period.

The term "dose" is used herein to mean administration of Compound I in one dosage form to the patient being treated. In some embodiments, the dose is a single oral formulation. In some embodiments, the dose is formulated as a tablet, a capsule, a pill, or a patch administered to the patient The term "effective daily dose" means the total amount of Compound I administered to a patient in need of therapy in a continuous, twenty-four (24) hour period. As a non-limiting example used herein solely to illustrate the meaning of the term, an effective daily dose of 90 mg shall mean and include administering a single dose of 90 mg in a twenty four hour period, administering two doses of 45 mg each within a twenty four hour period, and administering three doses of 30 mg each in a twenty four hour period, and so on. When administering Compound I in such a manner, i.e. more than once in a twenty four hour period, such administrations can be spread evenly through the twenty four hour period or even be administered simultaneously or nearly so.

The term "dose range" as used herein refers to an upper and a lower limit of an acceptable variation of the amount of agent specified. Typically, a dose of the agent in any amount within the specified range can be administered to patients undergoing treatment.

The term "treat" is used herein to mean to relieve, reduce or alleviate at least one symptom of a disease in a subject. For example, in relation to dementia, the term "treat" may mean to relieve or alleviate cognitive impairment (such as impairment of memory and/or orientation) or impairment of global functioning (overall functioning, including activities of daily living) and/or slow down or reverse the progressive deterioration in global or cognitive impairment.

The term "subject" is intended to include animals, which are capable of suffering from or afflicted with dementia associated with a CNS disorder, including without limitation neurodegenerative diseases such as Alzheimer's disease, Down's syndrome and cerebrovascular dementia, or any disorder involving, directly or indirectly, Alzheimer's disease. In certain embodiments, the subject is a human, e.g., a human suffering from, at risk of suffering from, or potentially capable of suffering from Alzheimer's disease or Alzheimer's disease-associated dementia, or Lewy body dementia.

The use of the terms "a" and "an" and "the" in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

The PET ligand used in the Positron Emission Topography study described in the Experimental Section is referred to as [$^{11}$C]LuPET and has the following structure:

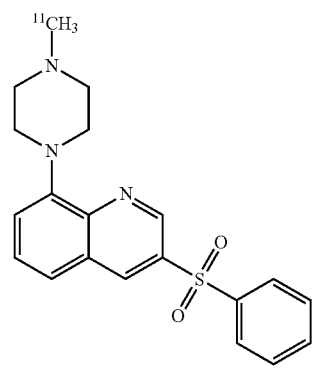

Pharmaceutically Acceptable Salts

The present invention also comprises salts of Compound I, typically, pharmaceutically acceptable salts. Such salts include pharmaceutically acceptable acid addition salts. Acid addition salts include salts of inorganic acids as well as organic acids. Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, et al., J. Pharm. Sci. 1977, 66, 2, the contents of which are hereby incorporated by reference.

Furthermore, Compound I and salts thereof may exist in unsolvated as well as in solvated forms with pharmaceutically acceptable solvents such as water, ethanol and the like.

Pharmaceutical Compositions

The present invention further provides a pharmaceutical composition comprising a therapeutically effective amount of Compound I and optionally a pharmaceutically acceptable carrier or diluent. Compound I may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

Suitable pharmaceutical carriers include inert solid diluents or fillers, sterile aqueous solution and various organic solvents. Examples of solid carriers are lactose, terra alba, sucrose, cyclodextrin, talc, agar, pectin, acacia, stearic acid and lower alkyl ethers of cellulose corn starch, potato starch, talcum, magnesium stearate, gelatine, lactose, gums, and the like. Other adjuvants or additives usually used for such purposes such as colourings, flavourings, preservatives etc. may be used provided that they are compatible with the active ingredients.

The pharmaceutical compositions formed by combining Compound I and the pharmaceutical acceptable carriers are then readily administered in a variety of dosage forms suitable for the disclosed routes of administration. The formulations may be presented in dosage form by methods known in the art of pharmacy.

Formulations of the present invention suitable for oral administration may be presented as discrete units such as capsules or tablets, each containing a predetermined amount of the active ingredient, and which may include one or more suitable excipients. The orally available formulations may be in the form of a powder or granules, a solution or suspension in an aqueous or non-aqueous liquid, or an oil-in-water or water-in-oil liquid emulsion. If a solid carrier is used for oral administration, the preparation may be tabletted, placed in a hard gelatine capsule in powder or pellet form or it can be in the form of a troche or lozenge.

Without limiting the scope of the invention, an example of an immediate release formulation of a once daily 30 mg dose of a pharmaceutically acceptable salt of Compound I is the following:

| | |
|---|---|
| Compound I monohydrochloride | 32.75 mg |
| Calcium Phosphohate Dibasic | 222.0 mg |
| Colloidal Silcon Dioxide NF (Aerosil 200) | 3.900 mg |
| Magnesium Sterate NF (Vegatable Grade) | 1.300 mg |

The formulation can be encapsulated in a Gelatin Capsule Size #3.

In a similar manner, pharmaceutical compositions may be prepared comprising the administration of Compound I wherein the dose ranges administered are between about 30 mg and about 60 mg.

Methods of Treatment

Provided herein is a combination therapy useful for the treatment of mild, moderate and severe Alzheimer's disease, as well as symptoms associated with mild to moderate Alzheimer's disease. As discussed below, the methods provided herein have a number of advantages.

The term "Alzheimer's disease" refers to a progressive disease of the human central nervous system. It is manifested by dementia typically in the elderly, by disorientation, loss of memory, difficulty with language, calculation, or visual-spatial skills, and by psychiatric manifestations. It is associated with degenerating neurons in several regions of the brain. The term "dementia" as used herein includes, but is not restricted to, Alzheimer's dementia with or without psychotic symptoms.

In a particular embodiment, the therapeutic methods provided herein re effective for the treatment of mild, moderate and severe Alzheimer's disease in a subject. Phases of Alzheimer's further include "moderately severe cognitive decline," also referred to as "moderate or mid-stage Alzheimer's disease;" "severe cognitive decline," also referred to as "moderately severe or mid-stage Alzheimer's disease;" and "very severe cognitive decline," also referred to as "severe or late-stage Alzheimer's disease." Moderately severe cognitive decline is characterized by major gaps in memory and deficits in cognitive function emerge. At this stage, some assistance with day-to-day activities becomes essential. In severe cognitive decline, memory difficulties continue to worsen, significant personality changes may emerge and affected individuals need extensive help with customary daily activities. Late stage Alzheimer's disease or very severe cognitive decline is the final stage of the disease when individuals lose the ability to respond to their environment, the ability to speak and, ultimately, the ability to control movement.

In another embodiment, the patient to be treated by the combination therapy of the invention has an MMSE score between 12 and 22. "MMSE" refers to the Mini-Mental State Examination used in the cognitive assessment community.

EXPERIMENTAL SECTION

| Table of Abbreviations | |
|---|---|
| 5-HT$_{2A}$ | 5-hydroxytryptamine 2A receptor |
| 5-HT$_6$ | 5-hydroxytryptamine 6 receptor |
| % | Percentage |
| AD | Alzheimer's Disease |
| AIC | Akaike information criterion |
| ANOVA | analysis of variance |
| A(T) | radioactivity concentration of the radioligand in a brain region at time t after the injection (units) |
| B$_{avail}$ | density of receptors available (unoccupied) to bind radioligand in vivo (nmol · L$^{-1}$ or nmol receptor · 1,000 cm$^{-3}$ tissue) |
| BP$_{ND}$ | in vivo binding potential (unitless) |
| ° C. | degrees Celsius |
| CIAS | Cognitive Impairment Associated with Schizophrenia |
| COV | coefficient of variation |
| CRO | contract research organization |
| C(t) | radioactivity concentration of the radioligand in plasma at time, t after the injection |
| D | BP$_{ND}$ post-dose |
| ECG | electrocardiogram |
| EC$_{50}$ | effective concentration that causes 50% of maximum occupancy |
| eg | exempli gratia (for example) |
| f$_{ND}$ | free fraction in nondisplaceable compartment (unitless) |
| FWHM | Full width at half maximum |
| g | Grams |
| H | Hour |
| HPLC | high-performance liquid chromatography |
| HRRT | high resolution research tomography |
| ie | id est (that is) |
| IRB | institutional review board |
| iv | intravenous |

-continued

Table of Abbreviations

| | |
|---|---|
| JHU | Johns Hopkins University |
| $K_1$ | rate constant for transfer from arterial plasma to tissue (mL/min/g or mL/min/cm$^3$) |
| $k_2$ | fractional brain-to-blood clearance rate constant of the radioligand (min-1) |
| $k_2'$ | efflux constant back to plasma; see Koeppe et al., 1991 |
| $k_3$ | association constant of the radioligand (min-1) |
| $k_4$ | dissociation rate constant of the radioligand (min-1) |
| $K_D$ | dissociation constant |
| μg | microgram |
| mCi | millicurie |
| mg | milligram |
| mL | milliliter |
| min | Minute |
| MRI | Magnetic Resonance Imaging |
| n | number |
| ng | Nanogram |
| OBD | optimum bed density, a trademark of Waters Corporation, Milford, MA |
| $O_{max}$ | maximum occupancy |
| OTCM | one tissue compartmental model |
| PET | Position Emission Tomography |
| pH | reverse logarithmic representation of relative hydrogen proton (H+) concentration |
| PI | Principal Investigator |
| PK | pharmacokinetic |
| po | per os, oral |
| PRGA | Plasma Reference Graphical Analysis |
| RO | receptor occupancy |
| $R^2$ | coefficient of determination for linear regression |
| SPGR | spoiled gradient, a type of data acquisition setting for MRI |
| T | tesla |
| TACs | time-(radio)activity curves |
| TTCM-UC | two-tissue compartment model approach with 5 parameters |
| TTCM-C | constrained two-tissue compartment model approach with 5 parameters |
| $v_0$ | vascular volume in tissue (mL/mL) |
| $V_{ND}$ | non-displaceable distribution volume, given as the $K_1$-$k_2$ ratio in TTCM-UC and TTCM-C (mL/mL) |
| $V_T$ | total volume of distribution (mL/mL) |
| VOI | volumes of interest |
| Brain structures | |
| Am | amygdala |
| Cb | cerebellum |
| Cg | cingulate cortex |
| CN | caudate nucleus |
| Fr | frontal cortex |
| Fs | fusiform gyrus |
| GP | globus pallidus |
| Hp | hippocampus |
| In | insula cortex |
| Oc | occipital cortex |
| Pa | parietal cortex |
| PH | parahippocampus |
| Pu | putamen |
| vS | ventral striatum |
| Th | thalamus |
| Tp | temporal cortex |

Example 1. Preparation of [$^{11}$C]LuPET

The precursor is 3-phenylsulfonyl-8-(piperazin-1-yl)quinoline ($C_{19}H_{19}N_3O_2S$; MW: 353.4) and is known and publically disclosed compound. The precursor was dissolved in acetonitrile and ransferred to a BioScan Autoloop System and reacted with [$^{11}$C]-Iodomethane prepared as follows. $^{11}CO_2$ prepared from bombardment of high purity nitrogen gas containing 0.5 to 1.0% oxygen with accelerated protons was reacted with hydrogen on a molecular sieve:nickel catalyst column at 380° C. to produce $^{11}CH_4$, which was reacted with iodine vapor heated to 740° C. to form $^{11}CH_3I$. [$^{11}$C]-Iodomethane was swept through a furnace containing silver triflate to convert the radiolabeled iodomethane to [$^{11}$C]-methyl triflate. [$^{11}$C]-methyl triflate was swept into the loop methylation system using helium gas at a flow rate of about 20 mL/min at ambient temperature. The accumulation of [$^{11}$C]-radioactivity in the loop was monitored with a local radiation monitor until the radioactivity reaches a plateau. The reaction mixture in the loop was allowed to remain at room temperature for 4.5 minutes. Crude [$^{11}$C]LuPET was purified by preparative high-pressure liquid chromatography (HPLC) using Waters XBridge Prep OBD C18 10 μm 10×150 mm column with 30% acetonitrile: 70% aqueous buffer (57 mM TEA adjusted to pH 7.2 with o-phosphoric acid) using a 10 mL/min flow rate. The [$^{11}$C]LuPET fraction as determined with an in-line radiometric detector was collected in a reservoir of water. The reservoir was pressurized to load the [$^{11}$C]LuPET onto the C18 Sep-Pak. The C18 Sep-Pak was then washed with 10 mL 0.9% Sodium Chloride for Injection. The [$^{11}$C] LuPET is eluted from the C18 Sep-Pak with 1 mL of Ethanol followed by 10 mL of 0.9% Sodium Chloride Injection, through a sterilizing 0.22 filter in a sterile, pyrogen-free vial that has been preloaded with 4 mL Sodium Chloride Injection.

Example 2. Positron Emission Topography Experiments (Parts A and B)

As the radioligand has not previously been dosed to humans it was initially evaluated in the human brain to identify an optimal method for quantification and validate the radioligand as a PET tracer (Part A). The primary objective of this study was to assess occupancy of the 5-HT$_6$ receptors after multiple oral doses of Compound I in healthy subjects using PET with [$^{11}$C]LuPET as the radioligand (Part B).

Subjects

Eight healthy male subjects (Age: 30.6±7.7 years; range: 22-44 years) participated in Part A, and sixteen healthy male subjects (Age: 32.3±7.6 years; range: 21-44 years) participated in Part B of this study.

PET Experiments

PET studies were performed on the GE Advance Tomograph (GE Medical Systems, Waukesha, Wis., USA). Subjects had one venous catheter for the radioligand injection, and one arterial catheter to obtain arterial blood samples for the determination of radioactivity in plasma. Then, subjects were positioned in the scanner with the head restrained with a custom-made thermoplastic mask to reduce the head motion during PET data acquisition. Then, a 10 minute attenuation scan was performed using a rotating $^{68}$Ge source for attenuation correction. Dynamic PET acquisition was then performed in a three-dimensional mode for 90 min following an intravenous bolus injection of [$^{11}$C]LuPET. A total of 30 PET frames were obtained (4×15, 4×30, 3×60, 2×120, 5×240, and 12×300 seconds). Arterial blood samples were collected at very short intervals (<5 s) initially and gradually prolonged intervals (every 15 min after 30 min) throughout the PET study for determination of plasma radioactivity. Selected samples taken at 0, 5, 10, 30, 45, 60, and 90 min were analyzed by HPLC for the presence of the radioligand and its radioactive metabolites as described elsewhere (Hilton et al., 2000).

In Part A, baseline scans were repeated on the same day (n=1) or separate days (n=7) ranging from 1 to 18 days apart to test reproducibility of PET outcome variables. A third scan was administered 5 hours after one single dose (10 mg) of olanzapine (n=5), utilized as a standard compound with high 5-HT$_6$ receptor affinity.

In Part B, one baseline scan was followed by one post-dose scan at 3 hours (3H scan) and at 10, 11, 27, or 51 hours (2nd post dose scan, P2) following a minimum of three days of oral dosing of Compound I.

Reconstruction of PET data: Emission PET scans were reconstructed using the back projection algorithm with a ramp filter using the software provided by the manufacturer correcting for attenuation, scatter, and dead-time (Kinahan and Rogers, 1989). The radioactivity was corrected for physical decay to the injection time. Each PET frame consisted of 128 (left-to-right) by 128 (nasion-to-inion) by 35 (neck-to-cranium) voxels. Expected spatial resolution in this reconstruction setting was 5.5 and 6.1 mm full width at half maximum (FWHM) in the radical and tangential directions, respectively, at 10 cm radius from the center of the field-of-view (Lewellen et al., 1996).

MRI Acquisition

On a separate occasion, a spoiled gradient (SPGR) sequence MRI was obtained on each subject for anatomical identification of the structures of interest using the following parameters: Repetition time, 35 ms; echo time, 6 ms; flip angle, 458°; slice thickness, 1.5 mm with no gap; field of view, 24×18 cm$^2$; image acquisition matrix, 256×192, reformatted to 256×256.

PET Data Analysis

Volumes of interest (VOIs): Cortical VOIs were automatically defined using Freesurfer software and combined into standard regions including: frontal (Fr), temporal (Tp), parietal (Pa), and occipital (Oc) cortices, fusiform gyrus (Fs), cingulate (Cg), and insula (In). Subcortical regions were defined with FIRST software (Patenaude et al., 2011) and manually adjusted on individual MRIs. Subcortical regions included putamen (Pu), caudate nucleus (CN), ventral striatum (vS), globus pallidus (GP), thalamus (Th), hippocampus (Hp), and amygdala (Am). VOIs were transferred from MRI to PET spaces following MRI-to-PET coregistration parameters given by SPM5 (Ashburner J, Friston 2003; Maes et al., 1997) to obtain time-activity curves (TACs) of regions. A total of 25 regions per scan were employed for methodological evaluations (Part A) while occupancy calculation was limited to Pu, CN, and vS (Part B).

Derivation of PET outcome variables: Primary PET outcome variables are total distribution volume, $V_T$ and binding potential, $BP_{ND}(=f_{ND} \cdot B_{avail}/K_D$ where $f_{ND}$ refers to the fraction of non-displaceable compartment, $B_{avail}$ stands for the density of available (unoccupied) 5-HT$_6$ receptors, and $K_D$ stands for the dissociation constant; Innis et al., 2007).

A set of standard plasma input methods were employed to identify the optimal method for derivation of regional distribution volume ($V_T$) for [$^{11}$C]LuPET including, a one tissue compartmental model (OTCM) with three parameters ($K_1$, and $k_2$'; See Koeppe et al., 1991 for the definitions, and $v_0$, tissue vascular volume), two tissue compartmental models with five parameters ($K_1$, $k_2$, $k_3$, $k_4$, and $v_0$; See Innis et al., 2007 for the definitions), without and with constraining the $K_1$-$k_2$ ratio (non-displaceable distribution volume, $V_{ND}$ (Abi-Dargham et al., 1994) to the cerebellum estimate (TTCM-UC and TTCM-C, respectively), and the plasma reference graphical analysis (PRGA; Logan et al., 1990). In TTCM-UC and TTCM-C, $BP_{ND}$ was given as the $k_3$-$k_4$ ratio. In PRGA, $BP_{ND}$ can be obtained as the region-to-Cb $V_T$ ratio less one, if it was confirmed that $V_T$ of Cb was not affected by the administration of Compound I. Metabolite-corrected plasma TACs were obtained by applying percent parent ligand time-profiles given by HPLC analysis to total plasma TACs, after interpolating at plasma sample times using the piecewise cubic Hermite interpolation implemented in Matlab (Mathworks, Cambridge, Mass., USA) and used in plasma input methods.

In addition, tissue reference methods, namely the multilinear reference tissue method with 2 parameters (MRTM2; Ichise et al., 2002) and reference tissue graphical analysis (RTGA; Logan et al., 1996) were applied. In RTGA, $k_2^R$ (the brain-to-blood clearance rate constant of Cb) was set at 0.076 min$^{-1}$, a mean $k_2$ value (across baseline scans) given by TTCM-UC.

Test and retest scans of Part A and baseline scans of Part B were used for this section.

Independent estimation of distribution volume of nondisplaceable compartment, $V_{ND}$: It has been shown that a scatter plot of $\Delta V_T$ (baseline minus post-dose) versus baseline $V_T$, often referred to as Lassen plot can yield 'theoretically correct' $V_{ND}$ as x-intercept of the regression line if the plot aligns linearly (Lassen et al., 1995; Cunningham et al., 2010). Note that this method yields one $V_{ND}$ value that is common to all regions of the baseline and post-dose scans. The use of Lassen plot may be granted for occupancy calculation only if the plot aligns linearly. $V_{ND}$ values given by the plot is used to evaluate whether $V_T$ of Cb may be used as an estimate of $V_{ND}$ (i.e., negligible 5-HT$_6$ receptors in Cb) in PRGA to obtain $BP_{ND}$ and receptor occupancy.

Test-Retest Variability: The reproducibility of $V_T$ and $BP_{ND}$ of [$^{11}$C]LuPET was evaluated using the test-retest variability (TRV) which is given by the following formula (e.g., Sudo et al., 2001):

$$TRV = \sum_{i=1}^{n} \frac{|V_{test} - V_{retest}|}{(V_{test} + V_{retest})/2} / n \qquad (1)$$

where $v_{test}$ and $v_{retest}$ refer to estimates of $V_T$ or $BP_{ND}$ of test and retest scans in the region, respectively. A number of papers employed a TRV of 10% as a criterion of radioligand acceptable reproducibility (Hirvonen et al., 2009). Therefore this level was used as reference in this report. Test and retest scans of Part A alone were used for this section.

Occupancy and occupancy-PK relationships: Occupancy of 5HT$_6$ receptors (RO in %) by Compound I (Part B) and olanzapine (Part A) was calculated with the following equation:

$$RO = \left(1 - \frac{BP_{ND}^D}{BP_{ND}^B}\right) \times 100 \qquad (2)$$

where superscripts indicate $BP_{ND}$ of baseline (B) and post-dose (D), respectively.

A single oral dose of 10 mg olanzapine has shown to result in a dopamine D2 receptor occupancy of approximately 60% in healthy male subjects (Nyberg et al., 1997). The olanzapine human in vitro receptor affinity for the 5-HT$_6$ and dopamine D$_2$ receptors are reported to be comparable with $K_i$ values of approximately 10 nM and 30 nM, respectively (Kroeze et al, 2003), so an at least comparable 5-HT$_6$ occupancy (=60%) could be expected at the 10 mg dose. As olanzapine has even higher affinity for the 5-HT$_{2A}$ receptor, some contribution from 5-HT$_{2A}$ to the measured total displacement following the olanzapine dose must be anticipated. In the striatum the density of 5-HT$_6$ is high (Woolley et al., 2004) and density of 5-HT$_{2A}$ is low (Pompeiano et al., 1994), and consequently the main contribution will be from displacement from 5-HT$_6$ receptors in this region.

The occupancy-PK (the concentration of Compound I in plasma) relationship was fitted by the following modified first-order Hill equation.

$$RO = \frac{PK \cdot O_{max}}{PK + EC_{50}} \quad (3)$$

where $O_{max}$ stands for the maximal attainable occupancy, and $EC_{50}$ refers to the PK that achieves 50% of $O_{max}$. Akaike information criteria (AIC; Akaike 1974; Burnham and Anderson 2004) was used to examine goodness of fit for compartmental models and for the examination of occupancy-PK relationships using Equation 3.

Results

The following results from Parts A and B refer to the figures in the Drawings of the Invention. Tissue TACs: On baseline scans, TACs of Pu and CN formed peaks before 10 min, and showed continued increases thereafter for the 90 min period (FIG. 1) while TACs of other brain regions reached respective peaks before 20 min and decreased monotonously thereafter. Cb showed the lowest accumulations of the radioactivity among brain regions. In post-dose scans, shapes of Pu and CN TACs became closer to TACs of other brain regions in a dose dependent manner (Panel B). Cb TACs remained relatively similar between baseline and post-dose scans.

FIG. 1: Time-activity curves (TACs) of selected brain regions (FIG. 1), as means of baseline scans of Part B (Panel A) and 3H post-dose (B) scans. Putamen and caudate nucleus showed distinctively high accumulation of radioactivity while cerebellum showed the lowest accumulation among brain regions. Total radioactive metabolites in plasma increased as a function of time after the tracer injection (FIG. 2, Panel A), reaching 69±9% at 90 min. 3H and 2nd-post dose scans showed indistinguishable HPLC time-profiles to baseline scans. Total and metabolite-corrected plasma TACs are shown in Panel B. Both formed peaks within 1 min (inlet), and declined mono-exponentially thereafter. Note that mean HPLC time-profile of 8 scans with successful HPLC were used in data analysis of Part A because HPLC was not successful in remaining 12 scans due to technical problems. HPLC time profiles of individual scans were used in Part B.

Figure 2:
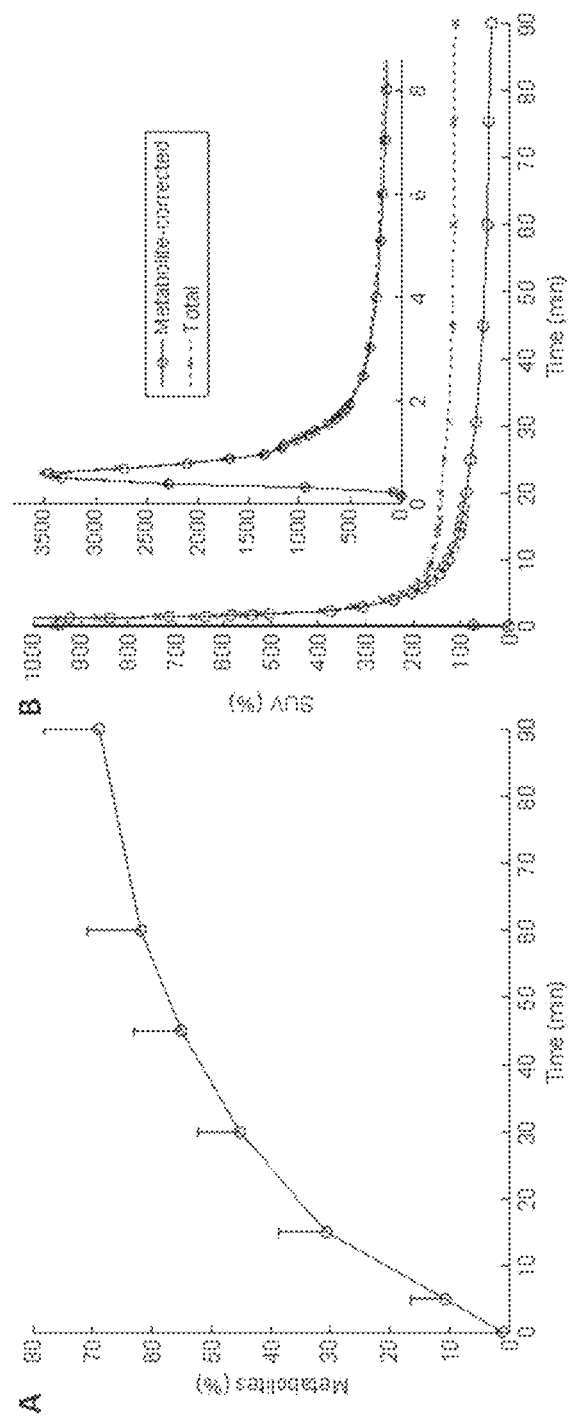
FIG. 2: Time-profile of total radioactive metabolites of [$^{11}$C]LuPET in plasma

FIG. 2: Time-profile of total radioactive metabolites of [$^{11}$C]LuPET in plasma (Panel A), averaged across baseline scans of Part B. Time activity curves (TACs), total and metabolite corrected in plasma (B) expressed in SUV as averages of baseline scans, limiting y-axis 1000 nCi/mL to display later parts TACs clearly (FIG. 2). The inlet was intended to show peaks clearly. Evaluation of methods for PET outcome variables: AIC supported TTCM over OTCM (i.e., OTCM showed higher AIC values than TTCM-UC or TTCM-C in 99.8% or 99.1% of total of 434 regions, respectively) suggesting that the blood-brain-transfer can be kinetically separated from the association-dissociation processes for [$^{11}$C]LuPET. Thus, OTCM was rejected for this radioligand. However, TTCM-UC and TTCM-C yielded outliers (defined arbitrarily as: $V_T$>20 mL/mL, the highest value by PRGA and $BP_{ND}$>15, 3 times greater than the highest value by PRGA) in 8.1% and 6.2% of total regions for $V_T$ and 7.2% and 4.4% for $BP_{ND}$. Therefore, it was concluded that TTCM-UC and TTCM-C were not sufficiently robust for estimation of $V_T$ and $BP_{ND}$ with [$^{11}$C]LuPET. PRGA plots approached asymptotes at least at 40 min and showed excellent linearity ($R^2$, coefficients of determination >0.93 in all regions). Further evaluations of PRGA are provided in the next two sections.

Between the two reference tissue methods, RTGA (=x) showed stronger correlation to PRGA (y=0.72·x+0.073; $R^2$=0.926) than MRTM2 (y=0.73·x+0.22; $R^2$=0.878), although both methods suffered underestimation of $BP_{ND}$ at high $BP_{ND}$ regions.

Figure 3:
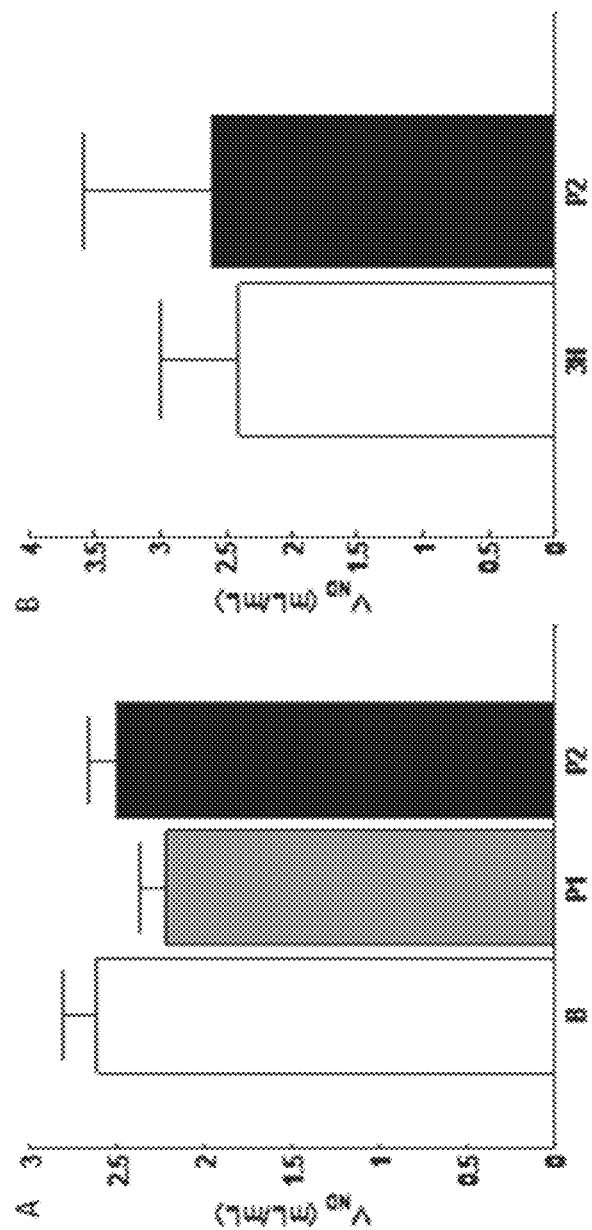
FIG. 3: Histograms (with SEM bars) of distribution volume ($V_T$) in cerebellum

Evaluation of Lassen plot and cerebellum $V_T$: Compared to the baseline scan, $V_T$ of Cb decreased at 3H scan (t=−3.09; p<0.01; paired t-test) and at second post-dose scan (t=−2.56; p<0.05) as shown in FIG. 3, Panel A. No statistical differences were observed between 3H and second post-dose scans (t=1.06; p>0.3). Lassen plot was linear ($R^2$>0.9) in all cases except for one case (baseline vs. 51 hour post-dose scans of Subject 502 who showed the lowest occupancy; $R^2$=0.501) whose $V_{ND}$ estimate was −0.39 mL/mL. $V_{ND}$ estimates remained unchanged between 3H and P2 scans (Panel B). However, the presence of the outlier eliminated the use of Lassen plot for occupancy calculation from this study. When the outlier was excluded, $V_T$ of Cb (=y) correlated with $V_{ND}$ given by Lassen plot (y=0.90·x+0.08; $R^2$=0.945) but was lower than $V_{ND}$ (t=−4.36; p<0.001). This finding ($V_T$ in Cb at 3H<$V_{ND}$ given by Lassen plot) suggested slight overestimation of $V_{ND}$ by the plot. Together with statistically significant but negligible differences (a mean difference of 0.39 mL/mL between baseline and 3H scans) relative to high $V_T$ values observed in striatum regions ($V_T$ ~10 mL/mL in target regions), evaluations in this section justified the use of PRGA for occupancy calculation with [$^{11}$C]LuPET using Cb as reference region.

Figure 4:
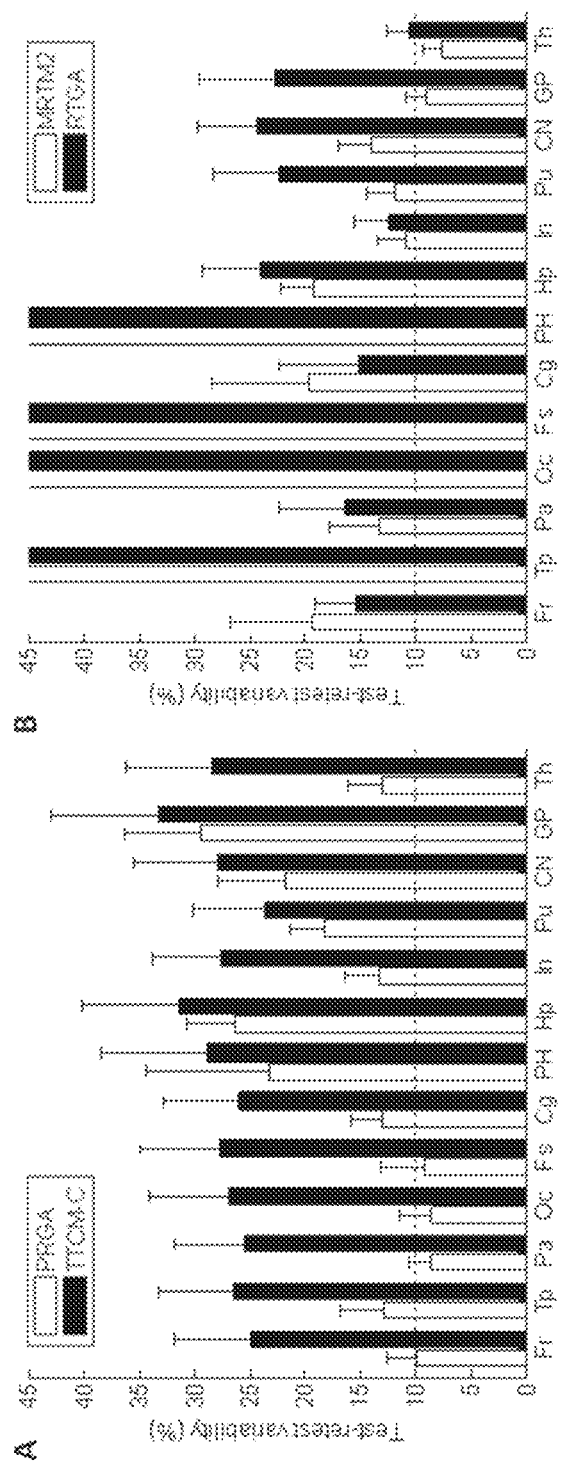
FIG. 4: Histograms (with SEM bars) of test-retest variability (TRV)

FIG. 3: Histograms (with SEM bars) of distribution volume ($V_T$) in cerebellum, Cb (Panel A) given by PRGA for baseline (B) and 3 hours (3H) and second post-dose (P2) scans, and distribution volume of non-displaceable compartment, $V_{ND}$ obtained by Lassen plots of regional $V_T$ of baseline and 3H scans (3H), and baseline and P2 scans (P2) (Panel B). Test-retest variability: PRGA showed low TRV values of $V_T$ (range: 12.7%-15.6%), achieving the desired 10% level in various regions, while TTCM-C (range: 13.3%-45.8%) showed higher TRV values. On $BP_{ND}$, TRV values of target regions (i.e., Pu and CN) were close to 20% by PRGA and slightly higher by TTCM-C (FIG. 4, Panel A). Tissue reference methods showed unacceptable TRV values in various cortical and subcortical regions (Panel B). However, RTGA showed TRV values in target regions that were very close to the 10% level.

FIG. 4: Histograms (with SEM bars) of test-retest variability (TRV) estimates of binding potential, $BP_{ND}$ for plasma input methods (Panel A) and reference tissue methods (B) in selected brain regions. Dotted horizontal lines indicate the 10% level which is often considered to be desirable level of TRV. Results of the method evaluation section including test-retest variability estimation indicated that PRGA is the most appropriate method for the derivation of $V_T$, $BP_{ND}$, and occupancy with [$^{11}$C]LuPET among widely recognized PET data analysis methods. Therefore, results obtained by PRGA are mainly presented hereafter. Results of RTGA are also presented as needed because the method section also indicated that RTGA may be usable when insertion of the arterial catheter and arterial blood sampling could be confounding factors, although the method may suffer from underestimation of $BP_{ND}$ at high $BP_{ND}$ regions. Regional values of $V_T$ given by PRGA and $BP_{ND}$ given by PRGA and RTGA are presented in FIG. 5 to indicate regional distributions of $V_T$ and $BP_{ND}$ in healthy male subjects in the studied age ranges.

Figure 5:
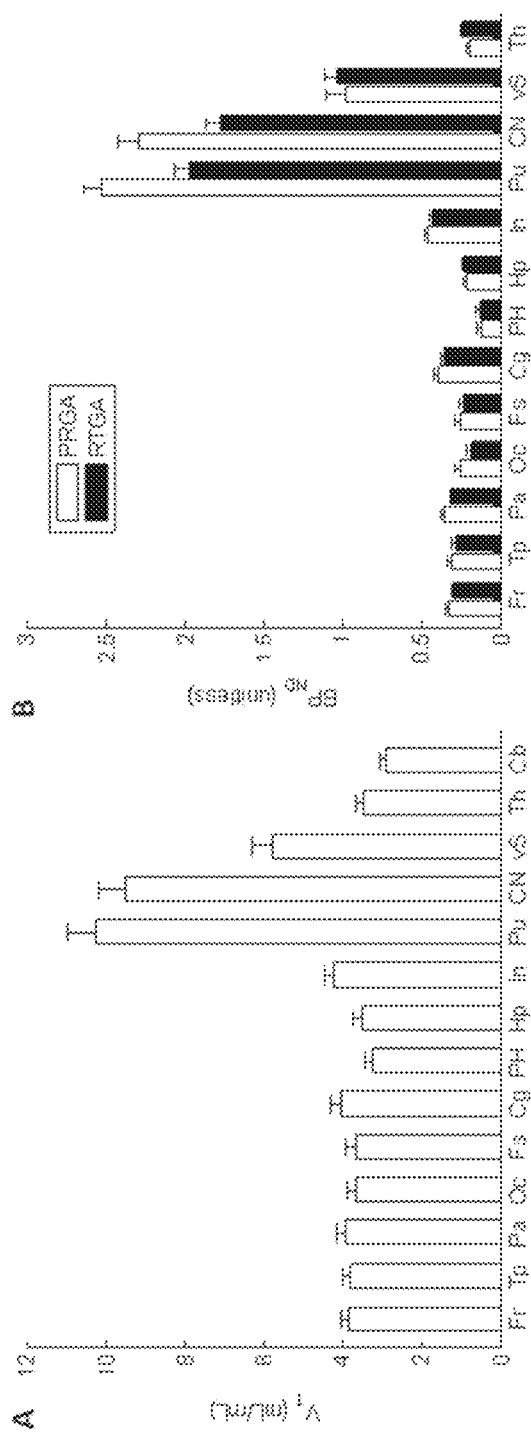
FIG. 5: Histograms (with SEM bars) of distribution volume $V_T$ in selected brain regions

FIG. 5: Histograms (with SEM bars) of distribution volume $V_T$ in selected brain regions (Panel A) in selected brain regions given by PRGA, and binding potential, $BP_{ND}$ given by PRGA and RTGA (B). Displacement of [$^{11}$C] LuPET binding by olanzapine: One dose of 10 mg olanzapine displaced binding of [$^{11}$C]LuPET about 80% across regions (FIG. 6), although some regional differences were observed. The findings were consistent with the expected displacement that was discussed in the occupancy and occupancy-PK relationship section of the method section. Note that relatively similar results were obtained whether test or retest scan was used as the baseline scan for the sake of displacement calculation.

Figure 6:
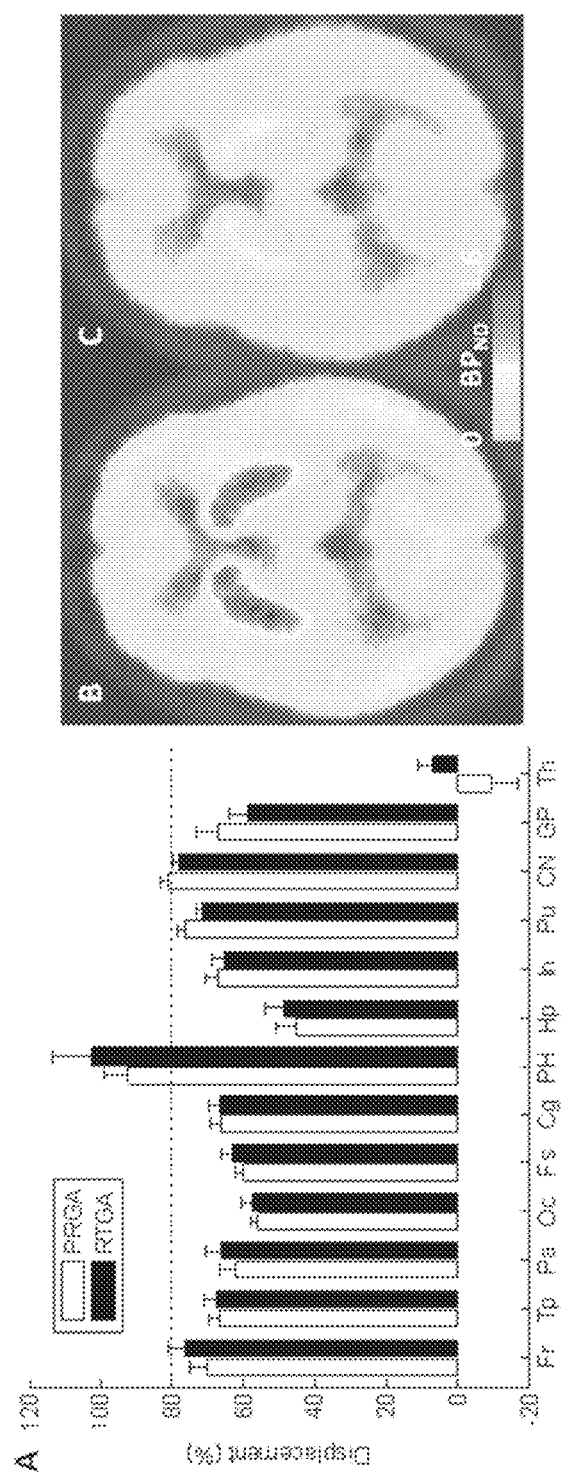
FIG. 6: Histogram of displacement (%) of [$^{11}$C]LuPET by one single dose of 10 mg of olanzapine in selected brain regions

FIG. 6: Histogram of displacement (%) of [$^{11}$C]LuPET by one single dose of 10 mg of olanzapine in selected brain regions (Panel A). Trans-axial images of binding potential $BP_{ND}$ at the level showing putamen (Pu) and caudate nucleus (CN) for baseline (B), and post-olanzapine (C) scans. Individual $BP_{ND}$ images were spatially normalized and averaged across subjects (n=5). Occupancy of 5-HT$_6$ receptors by Compound I and occupancy-PK relationships: Observed occupancy values for dosing schemes are shown in Table 2.

Figure 7:
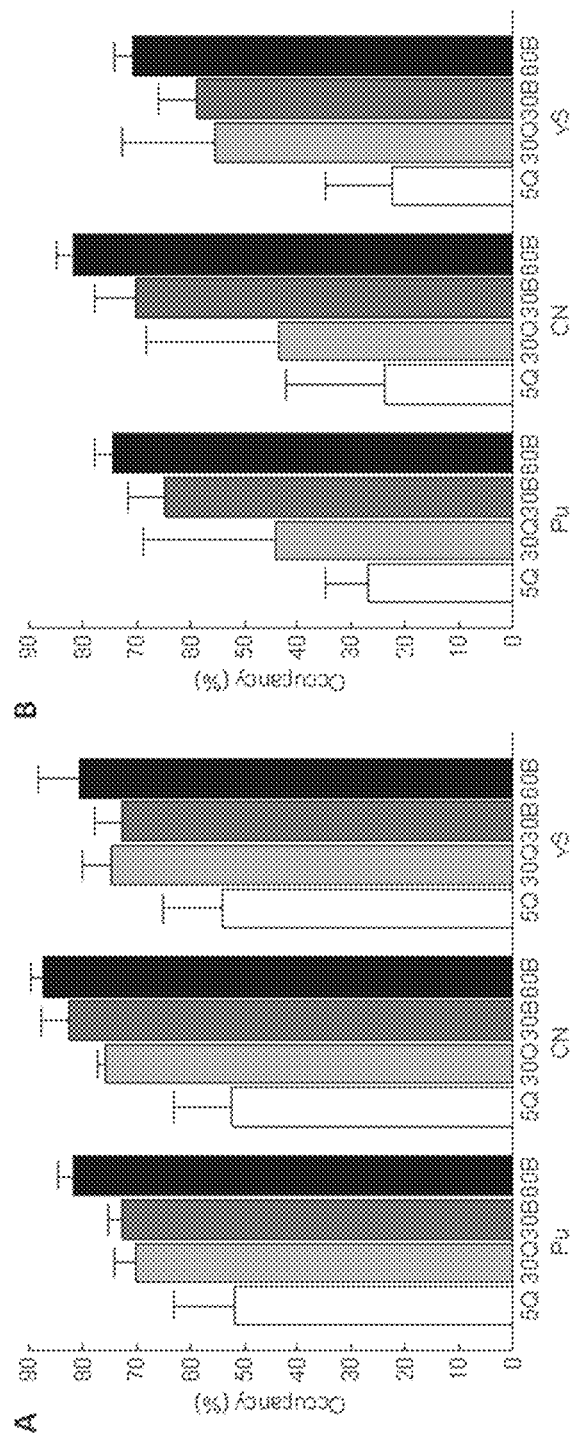
FIG. 7: Histograms (mean with SE bars) of occupancy of 5-HT$_6$ receptors by Compound I by dosing scheme for 3 hour and second post-dose time points.
Figure 8:
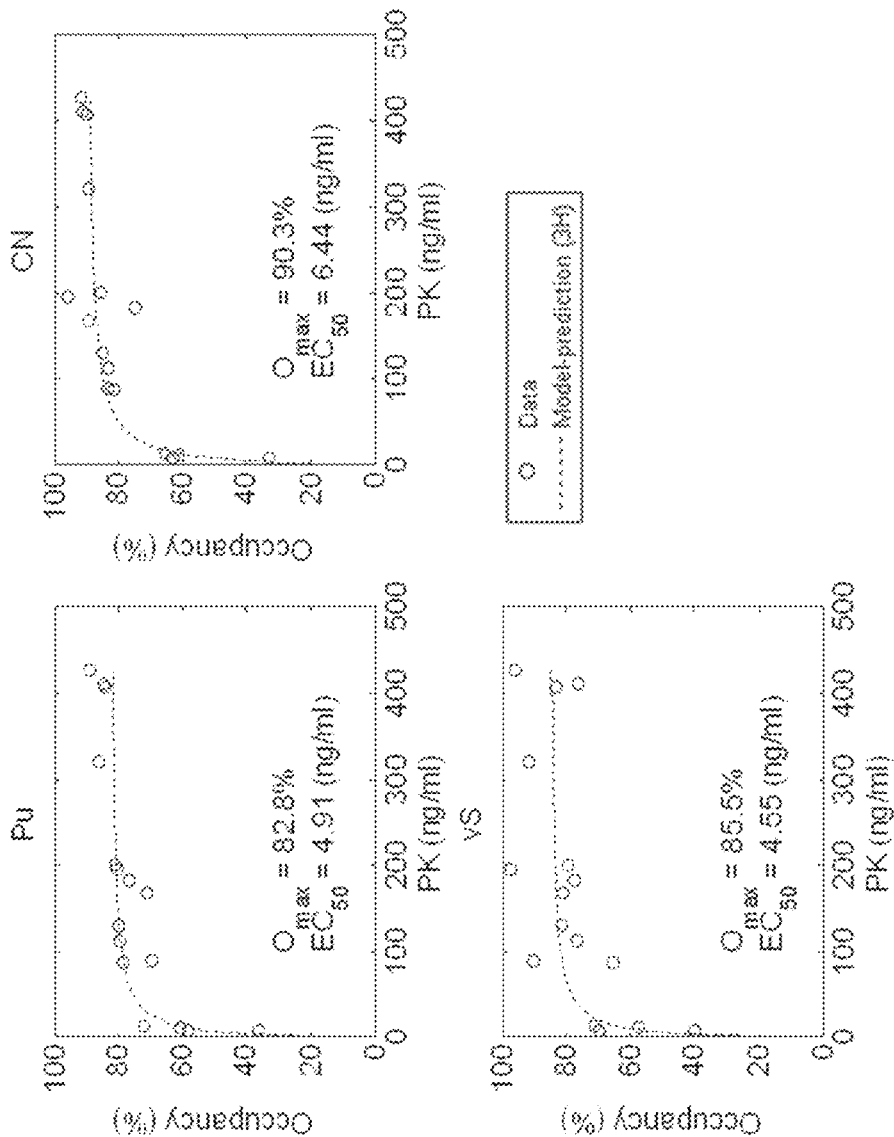
FIG. 8: Occupancy—PK plasma concentration of Compound I plots for putamen, caudate nucleus, and ventral striatum at 3 hour post-dose time point

FIG. 7. Occupancy-PK plots of 3H scans are shown in FIG. 8, together with the best fits of the plots by Equation 3 (i.e., model prediction). AIC supported a two parameter fit (i.e., estimation of both $O_{max}$ and $EC_{50}$) in favor of a one parameter fit (fixing $O_{max}$ at 100%) in three regions. Estimates of $O_{max}$, $EC_{50}$ and PK that is predicted to exert an 80% occupancy (80% RO) are listed in Table 2.

FIG. 7: Histograms (mean with SE bars) of occupancy of 5-HT$_6$ receptors by Compound I by dosing scheme for 3 hour (Panel A) and second (B) post-dose time points. Dosing schemes include 5 mg (5Q; Part B4) once daily or QD, 30 mg QD (30Q; Part B3), 30 mg b.i.d. (30B; Part B2), and 60 mg b.i.d (60B; Part B1). Scatter plots of occupancy (=y) versus concentrations of Compound I in plasma (mean from 30 to 90 min post-tracer injection) of 3H scans (FIG. 8) were fitted by Equation 3 assuming a 100% $O_{max}$ (Model 1; one parameter, $EC_{50}$ to estimate), and estimating both $O_{max}$ and $EC_{50}$ (Model 2). Model 2 was supported over Model 1 in Pu, CN, and vS by Akaike information criterion (AIC; The smaller the AIC value the better the fit) (Akaike 1974) and F-test comparing residual sums of squares (RSS) of the two models (Table 1).

FIG. 8: Occupancy—PK plasma concentration of Compound I (Lu AE58054) plots for putamen (Pu), caudate nucleus (CN), and ventral striatum (vS) at 3 hour post-dose time point. Model prediction curves (i.e., the best fits by Equation 3) are shown by dotted curves.

Figure 9:
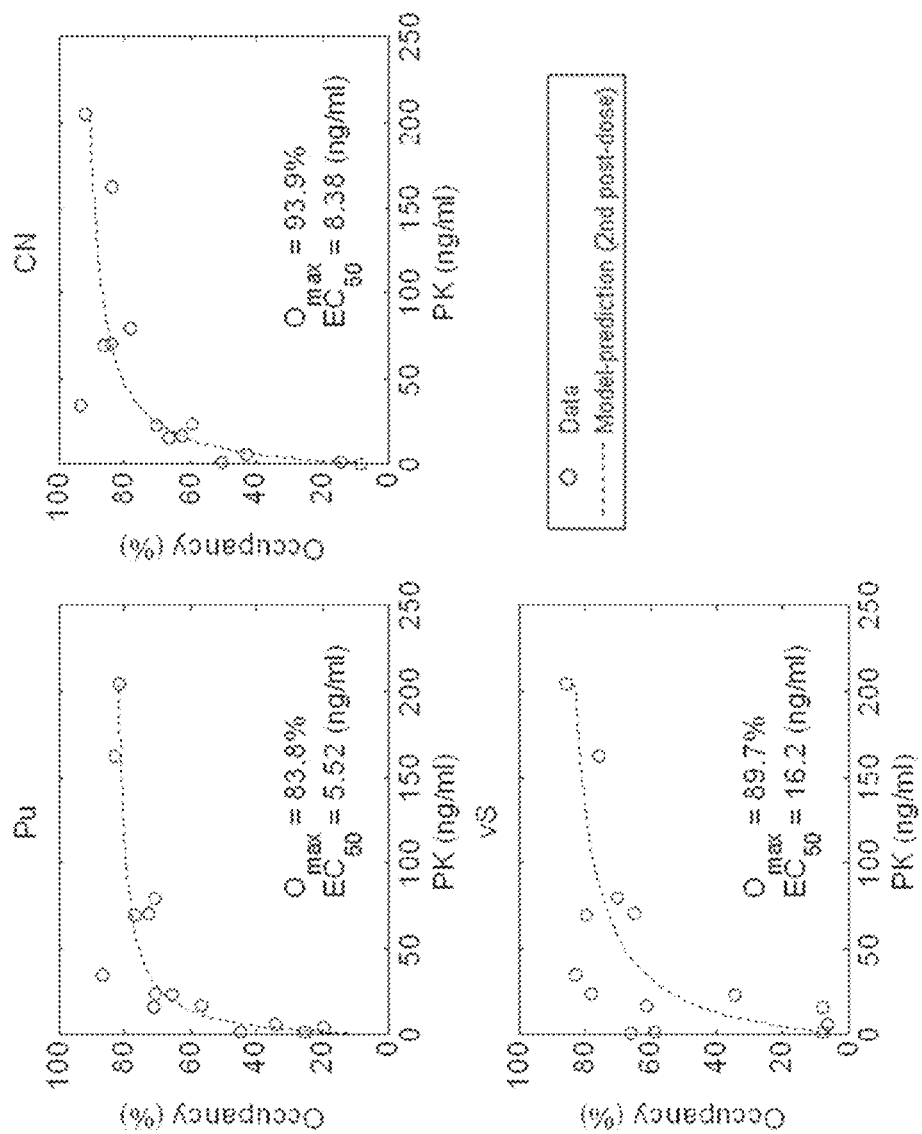
FIG. 9: Occupancy—PK plasma concentration of Compound I plots for putamen, caudate nucleus, and ventral striatum at second post-dose time points.

FIG. 9: Occupancy—PK plasma concentration of Compound I (Lu AE58054) plots for putamen (Pu), caudate nucleus (CN), and ventral striatum (vS) at second post-dose time points: Model prediction curves (i.e., the best fits by Equation 3) shown by dotted curves. The plots with all data points pooled were fitted better by Model 2 than by Model 1 in Pu and CN, suggesting that $O_{max}$ might be identified uniquely in these structures. Between 3H data points alone (red dotted curves) and the pooled data points (black dotted curves), model predicted curves were essentially identical in Pu and CN. Extrapolations of model prediction curves of P2 data alone (green dotted curves) also agreed with prediction curves of the pooled data.

The plots with all data points pooled were fitted better by Model 2 than by Model 1 in Pu and CN, suggesting that $O_{max}$ might be identified uniquely in these structures. Between 3H data points alone (red dotted curves) and the pooled data points (black dotted curves), model predicted curves were essentially identical in Pu and CN. Extrapolations of model prediction curves of P2 data alone (green dotted curves) also agreed with prediction curves of the pooled data. Accordingly, estimates of $O_{max}$ and $EC_{50}$ were consistent across 3H, P2 and pooled data sets. These findings were not conclusive for vS presumably reflecting unstable estimates of occupancy in this region.

RTGA which does not require plasma TACs yielded comparable estimates of $EC_{50}$ in Pu, Cn, and vS, but slightly lower estimates of $O_{max}$ than PRGA also lists PK values that were predicted to generate 80% occupancy, assuming that this occupancy level might generate optimal clinical effect. The PK values were about 120 ng/mL for CN and vS, and about 50 ng/mL for Pu by PRGA. The PK value was about 100 ng/mL for CN by RTGA but not available for Pu and vS due to the fact that estimates of $O_{max}$ were lower than 80% in these structures.

Figure 10:
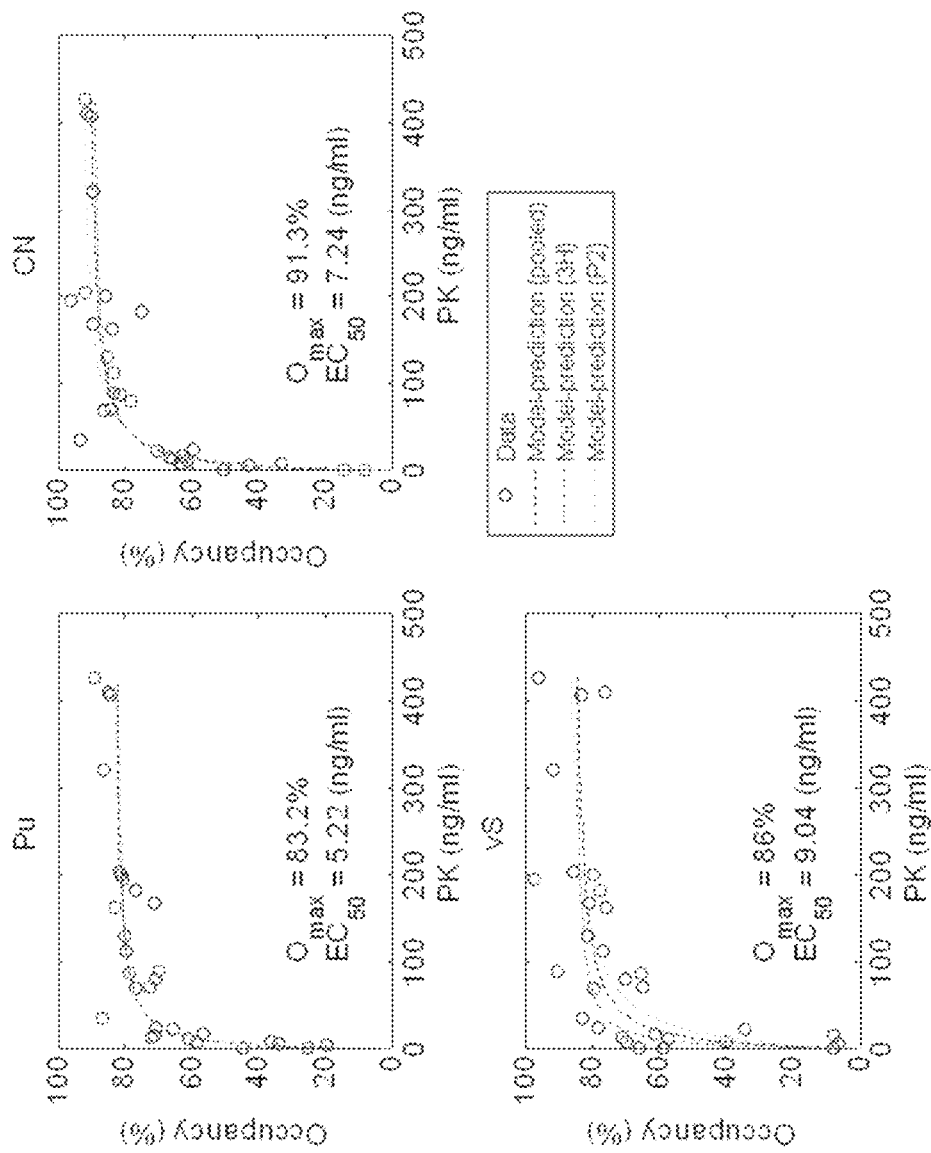
FIG. 10: Occupancy—PK plasma concentration of Compound I plots for putamen, caudate nucleus, and ventral striatum pooling two post-dose time points

FIG. 10: Occupancy—PK (plasma concentration of Compound I (Lu AE58054)) plots for putamen (Pu), caudate nucleus (CN), and ventral striatum (vS) pooling two post-dose time points. Model prediction curves (i.e., the best fits by Equation 3) are shown as indicated.

Figure 11:
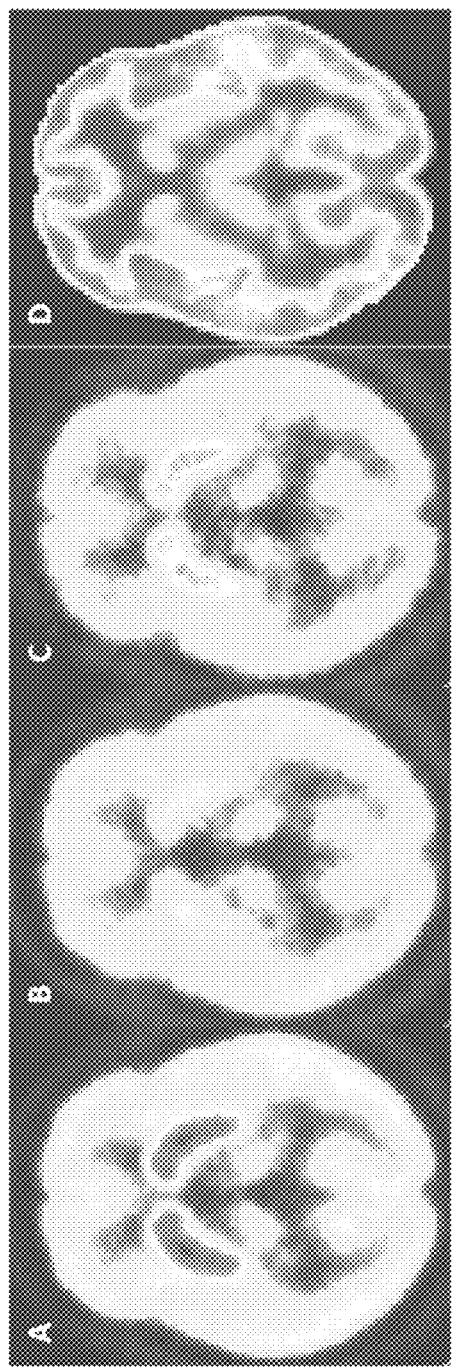
FIG. 11: Trans-axial images of binding potential at the level showing putamen and caudate nucleus for baseline, and 51 hours post-dose scans

FIG. 11: Trans-axial images of binding potential, $BP_{ND}$ at the level showing putamen (Pu) and caudate nucleus (CN) for baseline, and 51 hours (n=4; 30 mg one single dose only; C) post-dose scans: Trans-axial images of binding potential, $BP_{ND}$ at the level showing putamen (Pu) and caudate nucleus (CN) for baseline and 51 hours (n=4; 30 mg one single dose only; C) post-dose scans. A $BP_{ND}$ image of [$^{11}$C]MDL100,809 of healthy young subjects (n=8) are shown in Panel D for reference. Individual $BP_{ND}$ images were spatially normalized and averaged across members.

TABLE 1

Statistical evaluation of two models of the occupancy-PK equation (Equation 3)

| | Putamen (Pu) | | Caudate nucleus (CN) | | Ventral striatum (vS) | |
|---|---|---|---|---|---|---|
| | AIC Model 1 vs. 2 | F test | AIC Model 1 vs. 2 | F test | AIC Model 1 vs. 2 | F test |
| 3H | 86.56 >> 64.69 | 48.25** | 75.26 >> 66.26 | 13.84** | 86.78~75.45 | 18.19** |
| P2 | 82.20 > 79.66 | 4.06 | 83.87~85.44 | 0.38 | 100.36~102.13 | 0.36 |
| 3H + P2 | 166.82 >> 146.20 | 31.17** | 160.09 > 156.55 | 5.67* | 193.33~191.56 | 3.74 |

AIC: >> strongly supports Model 2; > supports Model 2; ~ not clearly different Degree of freedom for F-test were (1, 14), (1, 13), and (1, 29) for 3H, P2, and 3H + P2, respectively.
Asterisks indicate levels of significance: *for p < 0.05; **for p < 0.001.

The same plots for P2 scans are shown in FIG. 9. Both AIC and F-test did not support Model 2 over Model 1 potentially because sufficient numbers of 'close-to saturation' data points were not observed to estimate $O_{max}$ accurately at these later time points.

TABLE 2

Estimates of $O_{max}$, $EC_{50}$, and PK that is predicted to exert 80% occupancy

| | Putamen (Pu) | | | Caudate nucleus (CN) | | | Ventral striatum (vS) | | |
|---|---|---|---|---|---|---|---|---|---|
| | $O_{max}$ (%) | $EC_{50}$ (ng/mL) | 80% RO (ng/mL) | $O_{max}$ (%) | $EC_{50}$ (ng/mL) | 80% RO (ng/mL) | $O_{max}$ (%) | $EC_{50}$ (ng/mL) | 80% RO (ng/mL) |
| | | | | PRGA | | | | | |
| 3H | 82.8 | 4.9 | 137.8 | 90.3 | 6.4 | 50.1 | 85.5 | 4.6 | 66.5 |
| P2 | 83.8 | 5.5 | 116.7 | 93.9 | 8.4 | 48.0 | 89.7 | 16.2 | 133.5 |
| 3H + P2 | 83.2 | 5.2 | 131.7 | 91.3 | 7.2 | 51.1 | 86.0 | 9.0 | 121.0 |
| | | | | RTGA | | | | | |
| 3H | 77.5 | 5.4 | – | 85.2 | 6.7 | 102.8 | 78.2 | 4.6 | – |
| P2 | 76.6 | 6.0 | – | 87.1 | 9.0 | 101.5 | 72.1 | 4.9 | – |
| 3H + P2 | 77.3 | 5.8 | – | 85.7 | 7.8 | 108.4 | 76.5 | 5.2 | – |

The negative sign indicates that 80% occupancy may not be obtained.

Images of $BP_{ND}$ obtained by voxel-by-voxel application of PRGA are presented in FIG. 11 to visually display changes in $BP_{ND}$ after administration of Compound I.

Discussion

The methodological evaluation section of this study identified PRGA as the optimal method for deriving $V_T$, $BP_{ND}$, and occupancy from the radioligand PET data among widely recognized standard PET data analysis methods. The use of Cb as the reference region was justified for [$^{11}$C]LuPET because $V_T$ estimates of Cb were slightly lower (but with excellent correlations to) than $V_{ND}$ estimates given by Lassen plots for cases where the plot was successful.

It should be noted that TRV estimates of plasma input methods (TTCM and PRGA) could not be as accurate as they should be because of the use of mean HPLC time profiles for Part A scans due to unsuccessful HPLC in 60% of scans. Nevertheless, when individual scans' HPLC data were used in Part B, the goodness of fit (by means of AIC values) of occupancy-PK plots to the theoretical expectations (i.e., Equation 3) observed in this study were as good as AIC values observed in other receptor occupancy studies in our experience, which in turn ensures observed $O_{max}$ and $EC_{50}$ values obtained in Part B were accurate.

Distributions of $BP_{ND}$ in the human brain of [$^{11}$C]LuPET were strikingly different from $BP_{ND}$ distributions of [$^{11}$C]MDL100,907, a high-affinity antagonist ligand for 5-HT$_{2A}$ receptors (See FIG. 11): Pu and CN showed the highest $BP_{ND}$ with [$^{11}$C] LuPET but were relatively spared with [$^{11}$C]MDL100,907 while cortical regions showed high $BP_{ND}$ of [$^{11}$C]MDL100,907 but relatively low $BP_{ND}$ with [$^{11}$C]LuPET.

Occupancy-PK plots agreed with the first order Hill's equation (Equation 3) for 3H and P2 scans separately or with 3H and P2 scans pooled together. Furthermore, prediction curves of these three data sets were essentially identical. These findings indicated that occupancy-PK relationships agreed between P2 scans (post-dose duration range: 10-51 hours; PK range: 0.54-204 ng/mL) and 3H scans in which PK values fell within the PK range of P2 scans in 12 out of 15 subjects. Therefore it appeared that Compound I was associated with relatively fast dissociation from receptors and clearance from the brain (i.e., no evidence of prolonged binding).

Based on results of Pu and CN which showed convincing statistics, this study predicted that oral administration of Compound I would be associated with $O_{max}$ of about 90% and $EC_{50}$ of slightly greater than 6 ng/mL. It should be noted that CN showed about 10% higher estimates of $O_{max}$ than Pu. In fact, occupancy values were statistically higher for CN across all post-dose scans (t=2.09; p<0.05; df-30; paired t-test). Lastly, RTGA which does not require arterial blood sampling yielded comparable $EC_{50}$ values to more invasive PRGA. It was speculated that slight but influential blocking in the reference region (Cb) may explain the underestimation of $O_{max}$ by RTGA compared to PRGA. Thus, RTGA maybe applicable to drug occupancy studies in studying patient population on whom arterial blood sampling is not preferable. Finally, it should be mentioned that vS suffered uncertainty (i.e., AIC scores indicated worse fits by Equation 3) probably due to smaller volumes (~0.8 mL per side) than Pu and CN (>3 mL).

5-HT$_6$ receptor occupancy following administration of Compound I at 60 mg BID, 30 mg BID and 30 mg QD was high; i.e. >90%, >85% and ~80%, respectively, at $C_{max}$ and only decreased slightly 24 hours post dose.

In conclusion, this study estimated $O_{max}$ to be about 90% and $EC_{50}$ to be about 6.5 ng/mL with an oral administration of an amount Compound I. These estimates contribute to estimating occupancy of 5-HT$_6$ receptors that exerts optimal clinical efficacy when the optimal therapeutic doses and associated plasma concentrations of Compound I become available in its clinical applications.

Example 3. Population Pharmacokinetics Modeling & PK/PD Model 5-HT$_6$ Occupancy Simulation Using the data generated from the PET study of example 2, an objective of the modeling and simulation exercise was to estimate the 5-HT$_6$ receptor occupancies after multiple administrations of Compound I at once daily dosages in the range of 5.0-30 mg in an Alzheimer's population accordingly to age.

Population Pharmacokinetics (popPK) Model

Data from a Phase I study in elderly and data from the AD study (study 12936A) have shown that the clearance of Compound I is reduced in the elderly and hence elderly subjects having higher plasma concentrations compared to younger subjects for the same dose. This age effect has been incorporated in the PopPK model. In total, the dataset used in the popPK model consisted of 265 patients. The doses administered, single or multiple, were in the range of 9.0-300 mg.

PK/PD Model 5-HT$_6$ Occupancy 12 healthy subjects were included in the assessment of 5-HT$_6$ occupancy after multiple administrations of Compound I. The subjects were administered Compound I for at least three days at the doses 120 (60 BID), 60 (30 BID), 30 mg/day (QD) or 5 mg (QD) with four subjects in each dose cohort. In total three PET scans were performed per subject, the first at baseline, the second around $t_{max}$ on last day of dosing and the last in the interval 10-51 hours post dose on the last day of dosing.

Compound I plasma concentration versus 5-HT$_6$ receptor occupancy in the caudate nuclei region is shown in FIG. 11. The PK/PD relation was modelled with an $E_{max}$ model on the form Occ=$E_{max}$*Cp/(EC$_{50}$+Cp) where $E_{max}$ is the maximal occupancy, EC$_{50}$ the Compound I plasma concentration giving rise to half $E_{max}$ and Cp is the Compound I plasma concentration. In the clinical PET study, the occupancies for the second scan after baseline (performed 10-51 hours after last Compound I administration) did not obviously deviate more from the fitted plasma concentrations versus 5-HT$_6$ receptor occupancy curve than the occupancies for the first scan after baseline (performed around $C_{max}$). This indicates that no pronounced hysteresis or lag-time exists between PK and PD, which can be the case if for example the off-rate for the receptor is longer than the plasma elimination rate.

In order to allow for estimation of the inter-subject variability in the occupancy, non-linear mixed effect modelling was performed where the inter-subject variability was modelled as an exponential term on EC$_{50}$. $E_{max}$ and EC$_{50}$ for the caudate nucleus region were estimated to 91% and 6.5 ng/mL, respectively. The uncertainties of the estimated values were low, in terms of relative standard errors they were 1.1% ($E_{max}$) and 15% (EC$_{50}$). The reason for $E_{max}$ not reached 100% is may be due to the fact that the radioligand used ([$^{11}$C]LuPET) also binds to the 5-HT$_{2A}$ receptor. In the PK/PD simulations, $E_{max}$ was set to 100%.

PK/PD Model

An Alzheimer's population in terms of age to the one in the study 12936A was simulated (range 54-90 years and median 75 years). Steady-state plasma profiles of Compound I and corresponding 5-HT$_6$ receptor occupancies were simulated for the doses 5, 10, 15, 20, 25 and 30 mg/day and with 1000 patients per dose. The average 5-HT$_6$ receptor occupancy in the caudate nucleus region during one day at steady-state was estimated for each patient. The median, 5% and 95% percentiles were estimated from the individual values for each dose group. Hence, 90% of the patients will be in the interval between the 5% and 95% percentiles.

TABLE 3

Summary of steady state exposures in an elderly population (age 50-90 years[a]) simulated from the popPK model

| Gender | Dose (mg) | C$_{max}$ (ng/mL) | | | C$_{min}$ (ng/mL) | | | AUC (h · ng/mL) | | |
|---|---|---|---|---|---|---|---|---|---|---|
| | | Mean | Median | SD | Mean | Median | SD | Mean | Median | SD |
| Men | 30 QD | 173 | 136 | 120 | 100 | 61 | 116 | 3157 | 2251 | 2883 |
| | 60 QD | 370 | 286 | 273 | 225 | 134 | 265 | 6903 | 4821 | 6575 |
| | 30 TID | 529 | 376 | 510 | 433 | 273 | 503 | 11658 | 7928 | 12192 |
| Women | 30 QD | 185 | 148 | 123 | 97 | 56 | 117 | 3176 | 2247 | 2947 |
| | 60 QD | 393 | 310 | 280 | 217 | 124 | 268 | 6938 | 4812 | 6701 |
| | 30 TID | 543 | 385 | 528 | 427 | 262 | 519 | 11753 | 7920 | 12609 |

[a]mean 75 years, SD 7 years

Brief Discussion

Figure 12:
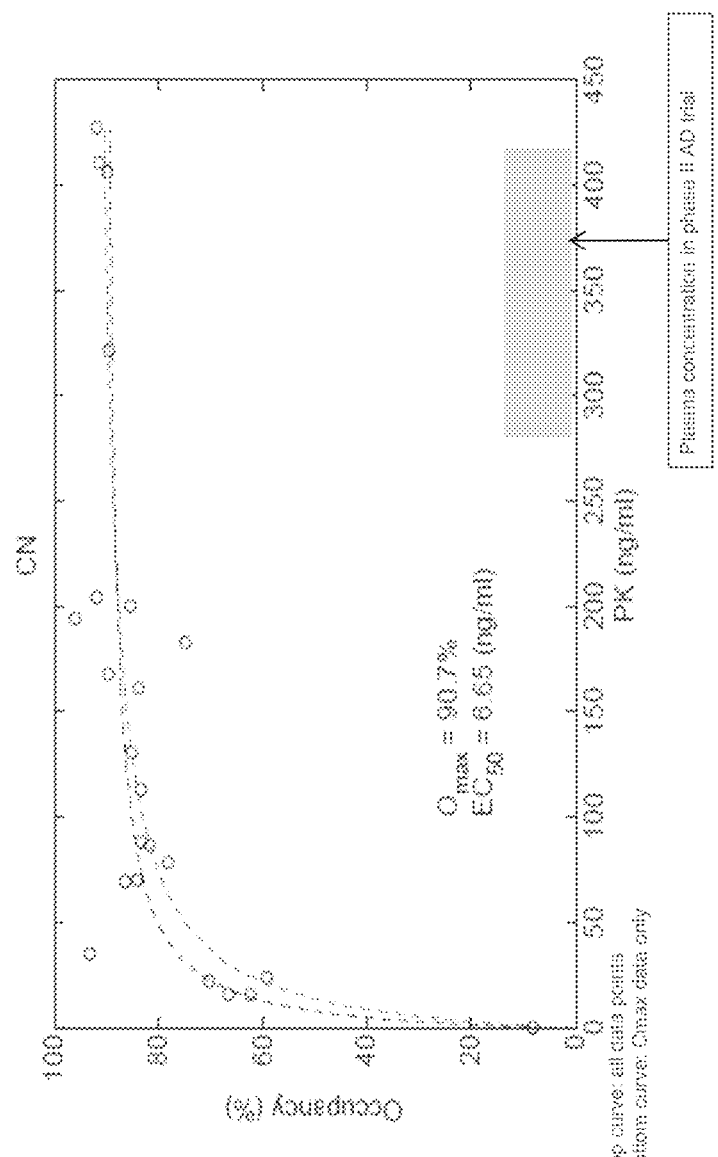
FIG. 12: Plasma concentrations of Compound I vs. 5-HT$_6$ receptor occupancy

Using the data from PK/PD model, FIG. 12 displays the projected correlation between 5-HT$_6$ receptor occupancy and plasma concentration of Compound I. The exposure (see highlighted range on X axis) given by the fixed dose of Compound I in the AD study shows that the subjects in the study experienced high receptor occupancy levels of the 5-HT$_6$ receptor.

Figure 13:
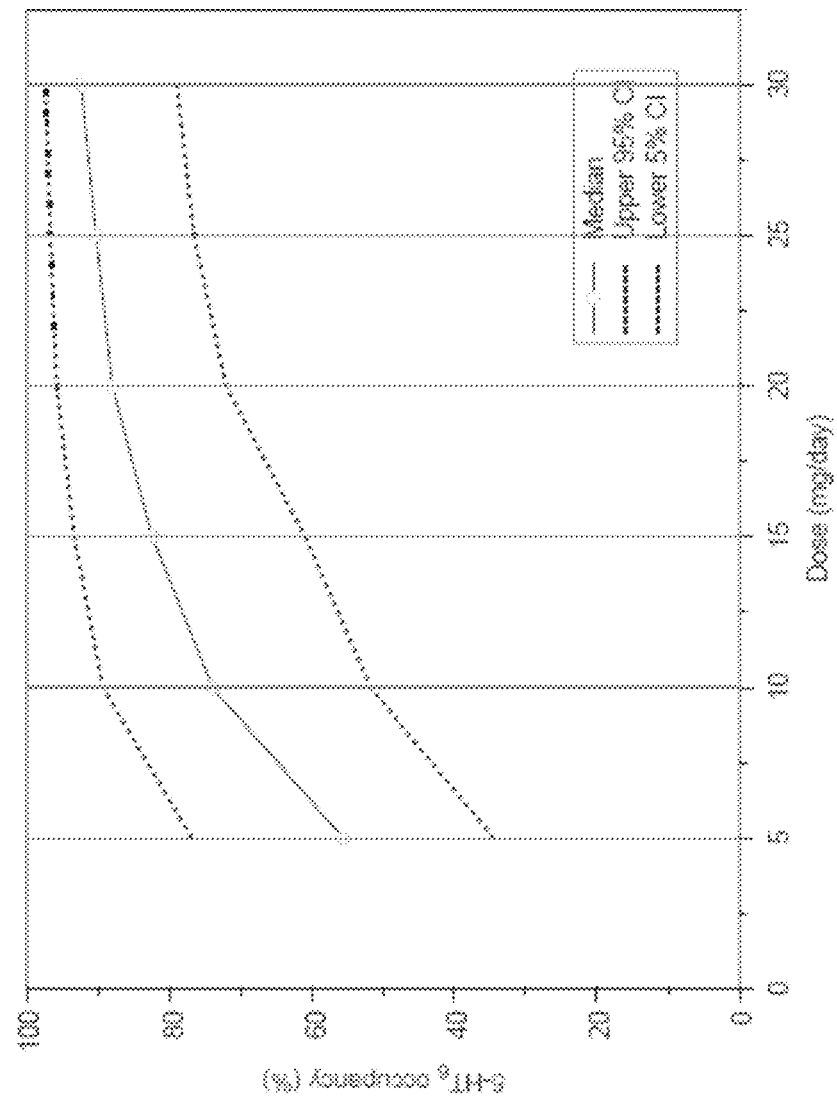
FIG. 13: Simulation of 5-HT$_6$ occupancy in caudate nucleus at steady-state for an AD population

FIG. 13 shows the simulated 5-HT$_6$ receptor occupancy in caudate nucleus_at steady-state for an Alzheimer's population for the doses 5.0-30 mg/day. The median occupancies range from 56% for 5.0 mg to 92% for 30 mg. Based on the results from the PET study, the plasma concentration of Compound I versus 5-HT$_6$ occupancy curve seems to be well described.

Thus, the data supports that finding of a daily dosing of an effective amount between about 30 and about 60 mg thereby improving patient compliance and avoiding complications seen in previous clinical trials.

What is claimed:

1. A method of treating dementia associated with Parkinson's disease by improving or augmenting the effect of an acetylcholinesterase inhibitor comprising administering an effective daily dose of N-[2-(6-fluoro-1H-indol-3-yl)ethyl]-3-(2,2,3,3-tetrafluoropropoxy)benzylamine or a pharmaceutically acceptable salt thereof to a patient in need of such treatment, wherein the effective daily dose administered to the patient is between about 30 and about 60 mg.

2. A method of treating dementia associated with Parkinson's disease as adjunctive therapy to treatment with an acetylcholinesterase inhibitor comprising administering an effective daily dose of N-[2-(6-fluoro-1H-indol-3-yl)ethyl]-3-(2,2,3,3-tetrafluoropropoxy)benzylamine or a pharmaceutically acceptable salt thereof to a patient in need of such treatment, wherein the effective daily dose administered to the patient is between about 30 and about 60 mg.

3. The method of claim 1, wherein patient is a human and the administered dose provides a blood plasma concentration of N-[2-(6-fluoro-1H-indol-3-yl)ethyl]-3-(2,2,3,3-tetrafluoropropoxy)benzylamine in a range of about 56 ng/mL to about 310 ng/mL at steady-state plasma level.

4. The method of claim 1, wherein the patient is a human and the administered dose provides a receptor occupancy of N-[2-(6-fluoro-1H-indol-3-yl)ethyl]-3-(2,2,3,3-tetrafluoropropoxy)benzylamine greater than or equal to about 90% at the 5HT-6 receptor at a steady-state plasma level.

5. The method of claim 2, wherein patient is a human and the administered dose provides a blood plasma concentration of N-[2-(6-fluoro-1H-indol-3-yl)ethyl]-3-(2,2,3,3-tetrafluoropropoxy)benzylamine in a range of about 56 ng/mL to about 310 ng/mL at steady-state plasma level.

6. The method of claim 2, wherein the patient is a human and the administered dose provides a receptor occupancy of N-[2-(6-fluoro-1H-indol-3-yl)ethyl]-3-(2,2,3,3-tetrafluoropropoxy)benzylamine greater than or equal to about 90% at the 5HT-6 receptor at a steady-state plasma level.

7. The method of claim 1, wherein the pharmaceutically acceptable salt is the hydrochloride.

8. The method of claim 1, wherein the dose is administered as an immediate release formulation.

9. The method of claim 1, wherein the acetylcholinesterase inhibitor is donepezil.

10. The method of claim 1, wherein the acetylcholinesterase inhibitor is rivastigmine.

11. The method of claim 1, wherein the effective daily dose is about 30 mg.

12. The method of claim 1, wherein the effective daily dose is about 40 mg or less.

13. The method of claim 1, wherein the effective daily dose is about 50 mg or less.

14. The method of claim 1, wherein the effective daily dose is about 60 mg or less.

15. The method of claim 2, wherein the pharmaceutically acceptable salt is the hydrochloride.

16. The method of claim 2, wherein the dose is administered as an immediate release formulation.

17. The method of claim 2, wherein the acetylcholinesterase inhibitor is donepezil.

18. The method of claim 2, wherein the acetylcholinesterase inhibitor is rivastigmine.

19. The method of claim 2, wherein the effective daily dose is about 30 mg.

20. The method of claim 2, wherein the effective daily dose is about 40 mg or less.

21. The method of claim 2, wherein the effective daily dose is about 50 mg or less.

22. The method of claim 2, wherein the effective daily dose is about 60 mg or less.

* * * * *

UNITED STATES PATENT AND TRADEMARK OFFICE
CERTIFICATE OF CORRECTION

Page 1 of 1

PATENT NO. : 9,789,085 B2
APPLICATION NO. : 15/194947
DATED : October 17, 2017
INVENTOR(S) : Ellen Schmidt et al.

It is certified that error appears in the above-identified patent and that said Letters Patent is hereby corrected as shown below:

On the Title Page

(71) Applicant should read: H. LUNDBECK A/S, Valby (DK)

(73) Assignee should read: H. LUNDBECK A/S, Valby (DK)

Signed and Sealed this
Fifth Day of December, 2017

Joseph Matal
*Performing the Functions and Duties of the
Under Secretary of Commerce for Intellectual Property and
Director of the United States Patent and Trademark Office*